(12) United States Patent
Perle et al.

(10) Patent No.: US 8,728,013 B2
(45) Date of Patent: May 20, 2014

(54) DEVICE AND METHOD FOR FITTING A PESSARY

(75) Inventors: Amir Perle, Haifa (IL); Elan Ziv, Ramat-Gan (IL); Idan Bauder, Carmiel (IL)

(73) Assignee: ConTIPI Medical Ltd., Caesarea (IL)

( * ) Notice: Subject to any disclaimer, the term of this patent is extended or adjusted under 35 U.S.C. 154(b) by 945 days.

(21) Appl. No.: 12/726,475

(22) Filed: Mar. 18, 2010

(65) Prior Publication Data

US 2010/0274159 A1 Oct. 28, 2010

Related U.S. Application Data

(60) Provisional application No. 61/161,079, filed on Mar. 18, 2009.

(51) Int. Cl.
*A61B 5/107* (2006.01)
*A61B 5/22* (2006.01)
*A61F 2/00* (2006.01)
*A61F 6/08* (2006.01)

(52) U.S. Cl.
CPC .............. *A61B 5/1076* (2013.01); *A61B 5/227* (2013.01); *A61F 2/005* (2013.01); *A61F 6/08* (2013.01)
USPC ...................................................... 600/591

(58) Field of Classification Search
CPC ...... A61B 5/1076; A61B 5/227; A61F 2/005; A61F 6/08
USPC ............................. 600/591, 587; 33/511, 512
See application file for complete search history.

(56) References Cited

U.S. PATENT DOCUMENTS

| | | | |
|---|---|---|---|
| 1,856,295 A | | 5/1932 | Sovatkin |
| 2,241,451 A | | 5/1941 | Fist |
| 2,394,140 A | * | 2/1946 | Biscow .......................... 606/119 |
| 2,456,806 A | * | 12/1948 | Wolffe ............................ 33/512 |
| 3,097,637 A | * | 7/1963 | Horton .......................... 600/588 |

(Continued)

FOREIGN PATENT DOCUMENTS

| | | | |
|---|---|---|---|
| GB | 2137499 | 10/1984 | |
| GB | 2426589 A | * 11/2005 | ............. A61B 5/107 |

(Continued)

OTHER PUBLICATIONS

Communication Pursuant to Rules 70(2) and 70a(2) EPC and Reference to Rule 39(1) EPC Dated Sep. 27, 2010 From the European Patent Office Re. Application No. 10156918.4.

(Continued)

*Primary Examiner* — Sean Dougherty
*Assistant Examiner* — Michael C Stout

(57) ABSTRACT

There is provided a device for measuring an inside shape of a vagina, including a device body, operationally connected to one or more movable cheeks, the cheeks movable in a direction substantially transaxially relative to the device body longitudinal axis, and a width indicator, for indicating a distance between opposite faces of the cheeks. There is provided a method for fitting a pessary including inserting a Pessary Caliber (PC) into a vagina, extending cheeks of the PC to press against sides of the vagina, measuring a distance between the cheeks, measuring how deep the PC is inserted into the vagina, and selecting a pessary size based, at least in part, on the measuring. Related apparatus and methods are also described.

11 Claims, 25 Drawing Sheets

(56) References Cited

U.S. PATENT DOCUMENTS

| | | | | |
|---|---|---|---|---|
| 3,164,009 | A * | 1/1965 | Marsh et al. | 73/789 |
| 3,467,088 | A * | 9/1969 | Robinson | 128/840 |
| 3,643,651 | A | 2/1972 | Cuadros | |
| 3,706,307 | A | 12/1972 | Hasson | |
| 4,016,867 | A * | 4/1977 | King et al. | 600/591 |
| 4,207,902 | A | 6/1980 | Krementsov | |
| 4,294,264 | A * | 10/1981 | Fischell et al. | 600/591 |
| 4,362,167 | A * | 12/1982 | Nicolai et al. | 600/591 |
| 4,566,465 | A * | 1/1986 | Arhan et al. | 600/591 |
| 4,611,603 | A | 9/1986 | Kelso et al. | |
| 4,685,474 | A | 8/1987 | Kurz et al. | |
| 5,010,892 | A * | 4/1991 | Colvin et al. | 600/587 |
| 5,197,465 | A * | 3/1993 | Montgomery | 128/207.29 |
| 5,379,754 | A * | 1/1995 | Tovey et al. | 600/109 |
| 5,833,605 | A * | 11/1998 | Shah | 600/393 |
| 6,033,359 | A * | 3/2000 | Doi | 600/117 |
| 6,039,701 | A * | 3/2000 | Sliwa et al. | 600/588 |
| 6,042,554 | A * | 3/2000 | Rosenman et al. | 623/2.11 |
| 6,081,737 | A * | 6/2000 | Shah | 600/393 |
| 6,322,526 | B1 * | 11/2001 | Rosenman et al. | 600/587 |
| 6,427,351 | B1 * | 8/2002 | Matthews et al. | 33/512 |
| 6,450,977 | B1 * | 9/2002 | Baxter-Jones | 600/591 |
| 6,981,988 | B1 * | 1/2006 | Kinsley | 623/8 |
| 7,007,396 | B2 * | 3/2006 | Rudko et al. | 33/512 |
| 7,189,234 | B2 * | 3/2007 | Zucherman et al. | 606/249 |
| 7,367,984 | B2 * | 5/2008 | Kulcinski et al. | 606/198 |
| 7,648,470 | B2 * | 1/2010 | Omata | 600/591 |
| 7,713,216 | B2 * | 5/2010 | Dubey et al. | 600/588 |
| 7,814,912 | B2 * | 10/2010 | George et al. | 128/207.14 |
| 8,012,106 | B2 * | 9/2011 | Mangiardi et al. | 600/587 |
| 2001/0039388 | A1 * | 11/2001 | Korotko et al. | 600/587 |
| 2002/0179093 | A1 * | 12/2002 | Adamkiewicz | 128/885 |
| 2003/0191416 | A1 * | 10/2003 | Rosenman et al. | 600/587 |
| 2004/0102722 | A1 * | 5/2004 | Naghavi | 600/587 |
| 2004/0225235 | A1 * | 11/2004 | Ben-Cnaan et al. | 600/591 |
| 2005/0061086 | A1 * | 3/2005 | Chappuis | 73/862 |
| 2006/0064038 | A1 * | 3/2006 | Omata et al. | 600/587 |
| 2006/0064039 | A1 * | 3/2006 | Griego et al. | 600/587 |
| 2006/0135887 | A1 * | 6/2006 | Sampson et al. | 600/591 |
| 2007/0106181 | A1 * | 5/2007 | Mangiardi et al. | 600/587 |
| 2007/0142752 | A1 * | 6/2007 | Kotmel et al. | 600/591 |
| 2007/0156068 | A1 * | 7/2007 | Dubey et al. | 600/588 |
| 2007/0239197 | A1 * | 10/2007 | Dubey et al. | 606/193 |
| 2008/0188774 | A1 * | 8/2008 | Dubey et al. | 600/588 |
| 2009/0062694 | A1 * | 3/2009 | MacDonald | 600/587 |
| 2009/0266367 | A1 * | 10/2009 | Ziv et al. | 128/834 |
| 2010/0249661 | A1 * | 9/2010 | Righini et al. | 600/587 |
| 2012/0109014 | A1 * | 5/2012 | Sherts et al. | 600/591 |
| 2013/0053863 | A1 * | 2/2013 | Juravic et al. | 606/119 |

FOREIGN PATENT DOCUMENTS

| | | | |
|---|---|---|---|
| WO | WO 2005/087154 | 9/2005 | |
| WO | WO 2006/097935 | 9/2006 | |
| WO | WO 2009/000056 | 12/2008 | |
| WO | WO 2009000056 A2 * | 12/2008 | A61B 5/107 |
| WO | WO 2009/130702 | 10/2009 | |

OTHER PUBLICATIONS

European Search Report and the European Search Opinion Dated Aug. 18, 2010 From the European Patent Office Re. Application No. 10156918.4.

Response Dated Mar. 21, 2011 to Communication Pursuant to Rules 70(2) and 70a(2) EPC and Reference to Rule 39(1) EPC of Sep. 27, 2010 From the European Patent Office Re. Application No. 10156918.4.

\* cited by examiner

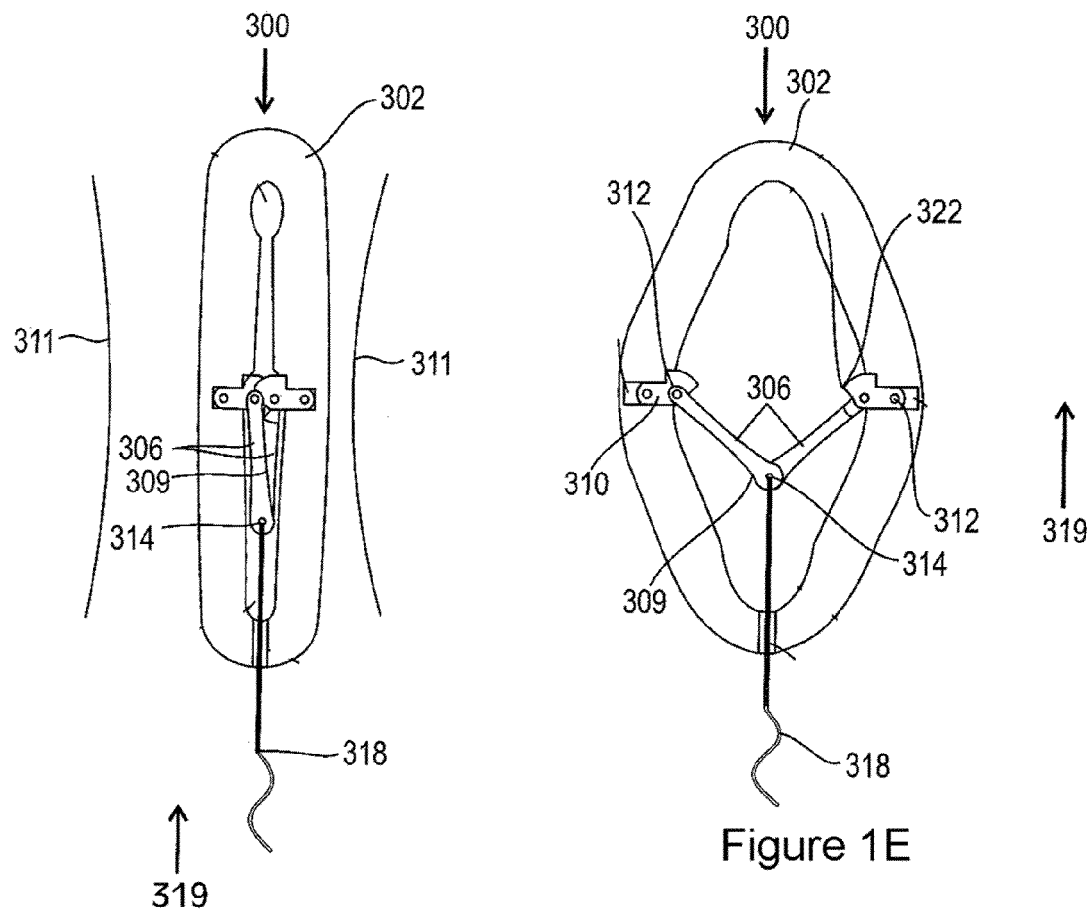
Figure 1D
Figure 1E
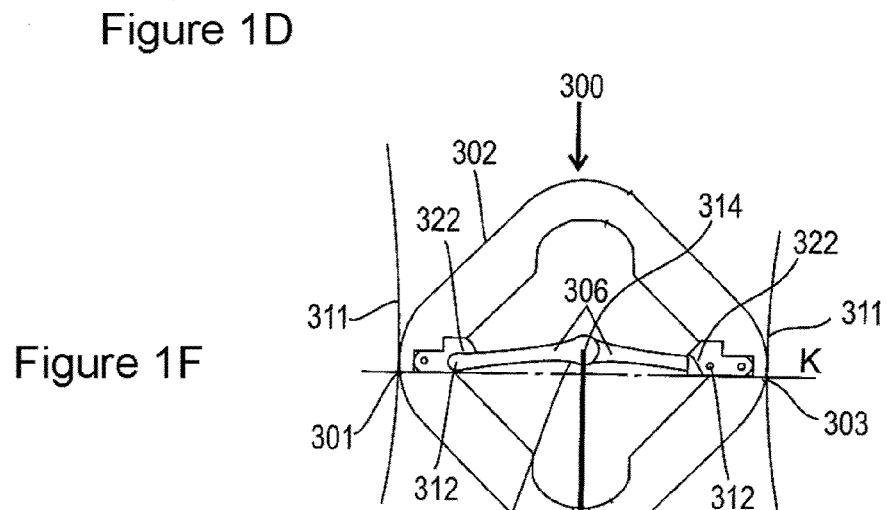
Figure 1F

FIGURE 5A  FIGURE 5B

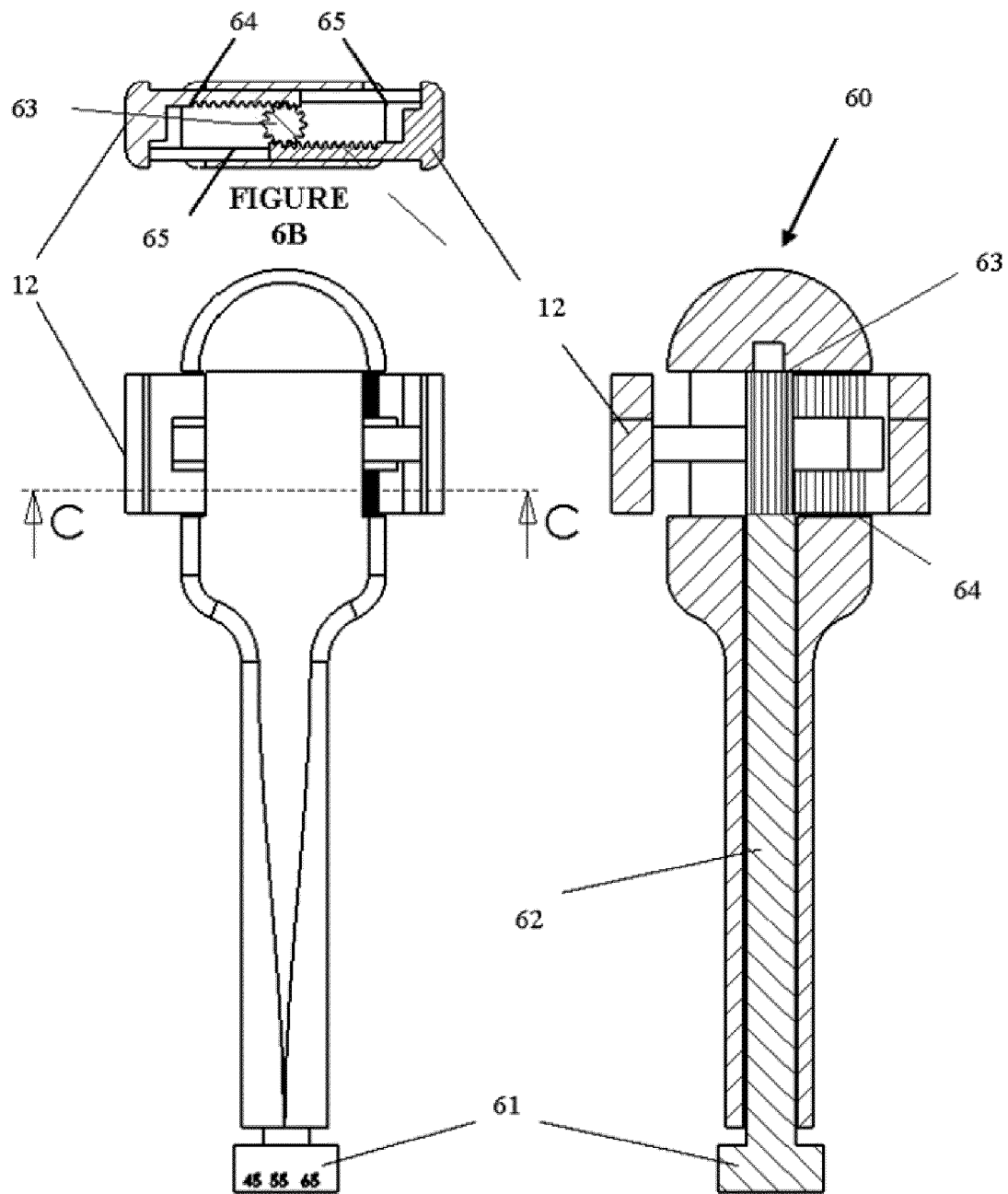

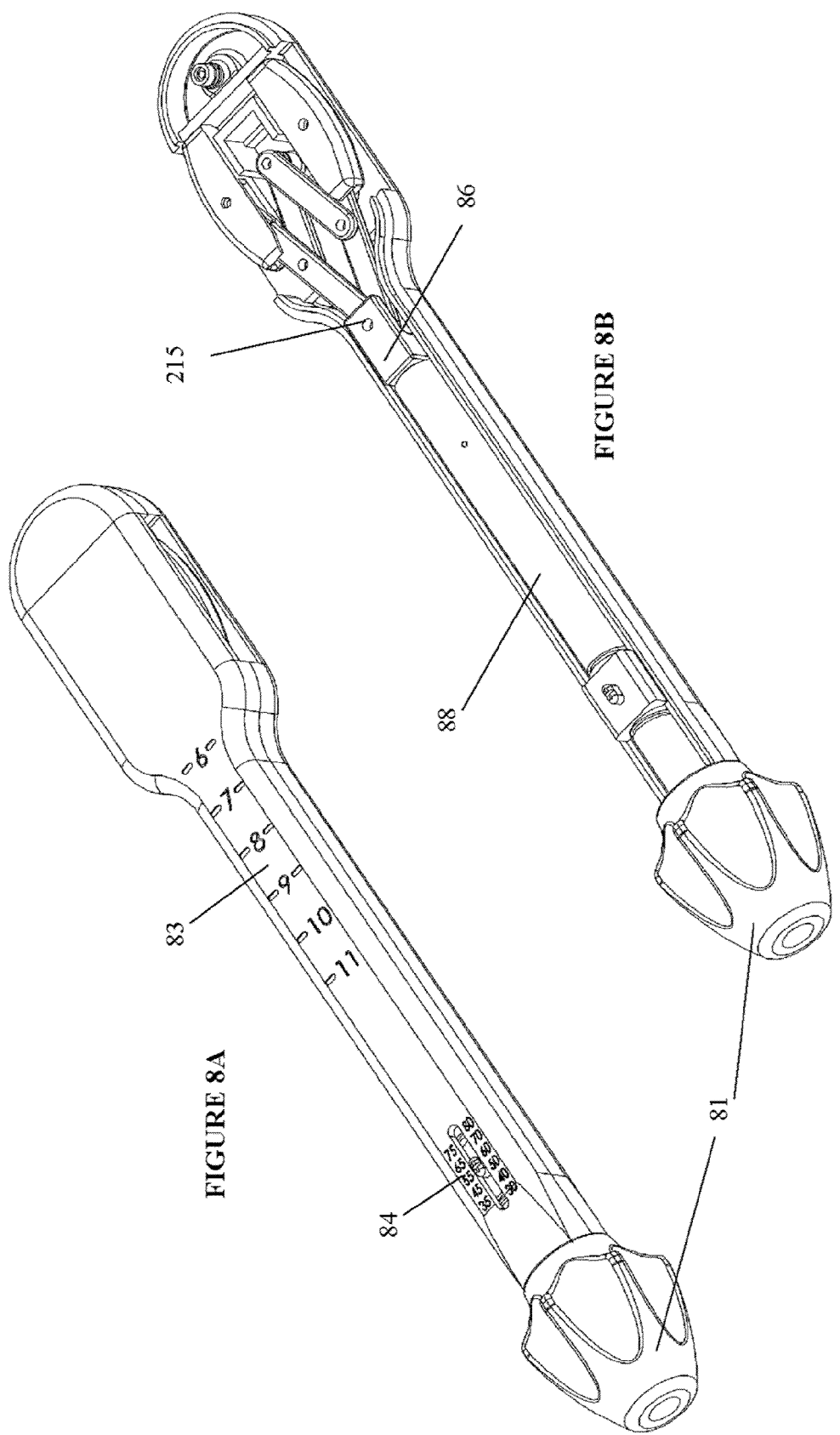

DEVICE AND METHOD FOR FITTING A PESSARY

RELATED APPLICATION/S

This application claims the benefit of priority under 35 USC 119(e) of U.S. Provisional Patent Application No. 61/161,079 filed on Mar. 18, 2009, the contents of which are incorporated by reference as if fully set forth herein.

FIELD AND BACKGROUND OF THE INVENTION

The present invention, in some embodiments thereof, relates to a device and methods for measuring dimensions of a vagina, and, more particularly, but not exclusively, to a device and methods for measuring dimensions of a vagina for purpose of fitting a pessary.

The pelvic floor (including the upper and lower vaginal support mechanisms and the internal and external anal sphincter) is a network of muscles, ligaments and other tissues that form a bowl like structure across the opening of the pelvis, holding up the pelvic organs. These muscles, together with their surrounding tissues, are responsible for keeping all of the pelvic organs (bladder, uterus and rectum) in place and functioning correctly.

Generally these internal organs are maintained in their position by a body of connective tissue and muscles that form a strong shelf on which all of the pelvic organs are situated. If these muscles are damaged or weakened through normal aging, child birth, pelvic surgery or trauma, the organs lose their normal positioning and the uterus and other pelvic contents may move into the vaginal cavity.

Pelvic Organ Prolapse (POP) is defined as a condition in which vaginal wall support is lost, and various pelvic organs prolapse into the vagina.

Symptoms of Pelvic Organ Prolapse are very bothering; depending on the type of POP experienced. For example, cases of rectocele may result in difficulty and/or pain associated with defecating, which would not normally be present in cases of vaginal vault prolapse. General symptoms associated with most forms of POP include, but are not limited to, Bulging of a lump out of the vagina, Feeling of pelvic heaviness, Pelvic and/or lower back pain, Stress Incontinence, Dyspareunia (pain during sexual intercourse), Excessive vaginal discharge, Recurrent bladder infections, Voiding difficulties up to retention, Difficulty emptying the bowels, Urgency & Urge Incontinence, Sexual discomfort & inability to reach orgasm, etc.

It is not uncommon for women to mistake prolapse symptoms for other conditions, particularly in cases where a noticeable bulge is not present. In circumstances where obvious symptoms are not present, women may not seek assistance for POP until their prolapse has already progressed to a clinically significant stage (e.g. the prolapsed organ is externally visible through the introitus).

There are two modalities of treatment—surgical and conservative. In some cases, surgery may not be the best treatment, particularly if the prolapse is manageable by conservative means. In the past, Estrogen Replacement Therapy (ERT) was considered to be an option of therapy, and so were Kegel exercises or Pelvic Floor Physiotherapy. It is now known that none plays a role in the therapy of such prolapses.

Pessaries, which are removable synthetic devices inserted into the vagina, are common non-surgical alternatives used to correct the fallen anatomical structure. Pessaries come in various formats to suit each specific form of prolapse, and are often used in conjunction with locally applied ERT.

With some types of pessaries, the patient may be taught to insert and remove the device by herself. In other types, patients have to be cared for in a medical office and generally will require regular visits every few weeks. Some women will be perfectly satisfied using a pessary as their only prolapse treatment. Other women use pessaries temporarily for relief of symptoms while they wait for a convenient time to have surgery. Some women even use pessaries after surgery if they still need a little extra support.

Additional background art includes:
PCT application PCT/IL2006/000346;
Published EP Patent Application 1727491 of Ziv;
U.S. Pat. No. 6,039,701 to Sliwa et al.
U.S. Pat. No. 4,611,603 to Kelso et al;
U.S. Pat. No. 4,207,902 to Krementsov;
U.S. Pat. No. 4,016,867 to King et al;
U.S. Pat. No. 3,706,307 to Hasson;
U.S. Pat. No. 3,643,651 to Cuadros;
U.S. Pat. No. 2,456,806 to Wolffe;
U.S. Pat. No. 2,241,451 to Fist; and
U.S. Pat. No. 1,856,295 to Sovatkin;

SUMMARY OF THE INVENTION

The present invention, in some embodiments thereof, includes a device for inserting into a vagina, for measuring dimensions of the vagina. The vagina may be wider within than at the entrance to the vagina, and/or may be gradually widening and/or have various width variation profiles. The device optionally has "cheeks" which are expandable, and which are expanded when the device is within the vagina. In some embodiments, the device measures depth of insertion into the vagina. The device optionally enables control of the cheek expansion from outside the vagina, and a reading of measurement parameters from outside the vagina.

The device is termed herein a Pessary Caliber, based on an example use for vagina measurements: a fitting of a pessary. The term "Pessary Caliber" is used throughout the present specification and claims interchangeably with the term "vagina measurement device" and its corresponding grammatical forms.

According to an aspect of some embodiments of the present invention there is provided a device for measuring an inside shape of a vagina, including a device body, operationally connected to one or more movable cheeks, the cheeks movable in a direction substantially transaxially relative to the device body longitudinal axis, and a width indicator, for indicating a distance between opposite faces of the cheeks.

According to some embodiments of the invention, further including a depth indicator, for indicating a depth of insertion of the device into the vagina.

According to some embodiments of the invention, further including a force gage, for measuring a force by which the cheeks are pressing against the inside of the vagina.

According to some embodiments of the invention, the cheeks are shaped so as to prevent damage to vagina walls when pressing against the inside of the vagina.

According to some embodiments of the invention, the one or more movable cheeks include at least two cheeks, each movable in an opposite direction substantially transaxially to the device body longitudinal axis.

According to some embodiments of the invention, the one or more movable cheeks include at least two cheeks, each at a different axial position along the device body longitudinal axis.

According to some embodiments of the invention, the one or more movable cheeks are operationally connected to the device body by linkage of a mechanical arm for each cheek.

According to some embodiments of the invention, the one or more movable cheeks are operationally connected to the device body by a rack and pinion mechanism.

According to some embodiments of the invention, a rod is operationally connected to the mechanical arms, and pushing the rod causes the mechanical arms to push the movable cheeks substantially outward.

According to some embodiments of the invention, a rod is operationally connected to the mechanical arms, and rotating the rod in one direction causes the mechanical arms to push the movable cheeks substantially outward, while rotating the rod in an opposite direction causes the mechanical arms to pull the movable cheeks substantially inward.

According to some embodiments of the invention, the one or more movable cheeks are mounted on pistons, and the outward and inward movement is achieved by liquid pressure.

According to some embodiments of the invention, the one or more movable cheeks are mounted on pistons, and the outward and inward movement is achieved by gas pressure.

According to some embodiments of the invention, the width is indicated in terms of a pessary size.

According to some embodiments of the invention, the depth is indicated in terms of a pessary size.

According to some embodiments of the invention, the device is packaged in a kit together with a pessary. According to some embodiments of the invention, a cross sectional area of the cheeks which abuts the vaginal walls is substantially equal to a cross sectional area of the pessary which abuts the vaginal walls. According to some embodiments of the invention, a shape of a portion of the cheeks which abuts the vaginal walls is substantially similar to a shape of a portion of the pessary which abuts the vaginal walls.

According to some embodiments of the invention, a maximum diameter of the device in a direction perpendicular to the device body longitudinal axis is small enough to fit into a small sized vagina, and the maximum diameter to which the device may grow by extending the cheeks is large enough to press upon opposite sides of a large vagina.

According to an aspect of some embodiments of the present invention there is provided a method for fitting a pessary including inserting a Pessary Caliber (PC) into a vagina, extending cheeks of the PC to press against sides of the vagina, measuring a distance between the cheeks, measuring how deep the PC is inserted into the vagina, and selecting a pessary size based, at least in part, on the measuring.

According to some embodiments of the invention, the measuring includes measuring a force of the cheeks on the sides of the vagina, and the selecting is further based, at least in part, on the force.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTIONS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1D-1F are simplified illustrations of an example of a Pessary for treating pelvic organ prolapse;

FIGS. 5A-5C are simplified illustrations of yet another alternative embodiment of a PC device;

FIGS. 6A-6D are simplified illustrations of still another alternative embodiment of a PC device;

FIGS. 8A-8D are simplified illustrations of still another alternative embodiment of a PC device;

DESCRIPTION OF SPECIFIC EMBODIMENTS OF THE INVENTION

Figure 1A:
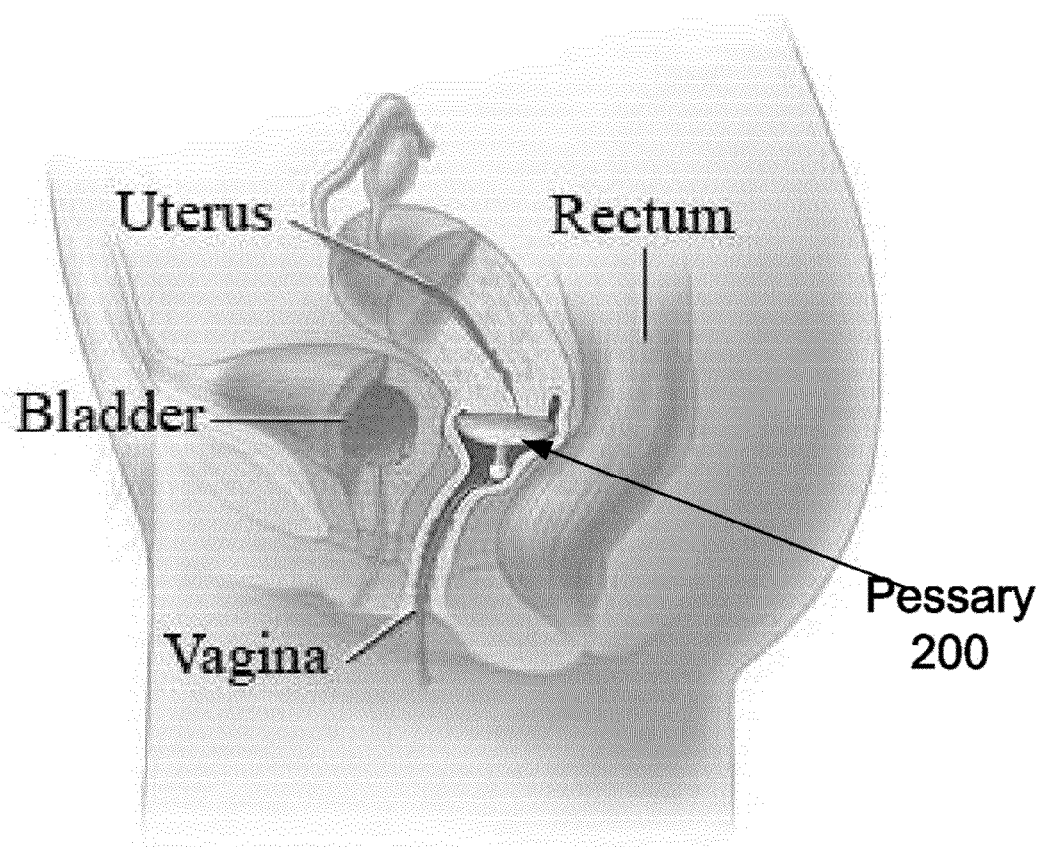
FIG. 1A is a simplified illustration of one example of a Pessary in place in a vagina.

The present invention, in some embodiments thereof, relates to a device and methods for measuring dimensions of a vagina, and, more particularly, but not exclusively, to a device and methods for measuring dimensions of a vagina for purpose of fitting a pessary.

It is noted that fitting a pessary according to prior art is a trial and error procedure, wherein a caretaker makes an estimate as to a proper pessary size, then fits the size guessed at, and requires the patient to try it on. An accurate measurement of size, and optionally shape, and optionally force applied against vaginal walls, can aid in making a better first fit, speed up the fitting process, and decrease discomfort of the patient.

Advanced types of pessaries are presently in development, which have a form designed to provide specific treatments, such as, by way of a non-limiting example, treating urinary incontinence. It would be useful if pessary fitting took into account vaginal measurements at locations where the pessary is intended to be located, rather than a general maximal size of a vagina.

The present invention, in some embodiments thereof, provides measurements of vaginal diameter, and/or maximal extent, if desired at several different depths into the vagina, while measuring the depth.

The present invention, in some embodiments thereof, provides measurements of force applied against the vaginal walls, if desired at several different depths into the vagina, while measuring the depth. The force may be translated into pressure, when taking into account the area upon which the force is applied.

When operating a device for fitting a pessary constructed according to embodiments of the present invention, some embodiments of the method for using the device include measuring vaginal diameter at a pre-determined force and/or pressure, providing an answer to a question of "what size is right for the force and/or pressure", and some embodiments of the method for using the device include measuring force and/or pressure at a pre-determined vaginal diameter, providing an answer to a question of "is the diameter right for providing the force and/or pressure".

It is noted that different treatments provided by inserting a pessary, such as, by way of a non-limiting example, treatments for the various problems associated with Pelvic Organ Prolapse, require exerting different forces at different locations in the vagina.

It is noted that for stretching walls of the vagina, and treating prolapse, force is typically the measurement to be used. For patient comfort and for pessary anchoring, pressure is typically the measurement to be used.

The present invention, in some embodiments thereof, provides measurements of vaginal diameter in a substantially trans-axial direction, allowing the person measuring to take measurements at different depths, independent of the shape of the vagina. For example, if the vagina is narrower at the back than at the front, both back and front measurements will produce true readings. For example, if the vagina is wider at the back than at the front, both back and front measurements will still produce true readings.

It is to be appreciated that in cases where a pessary is used for treatment, the pessary is often intended to push against the vaginal walls. Optionally, the pessary caliber should produce a substantially equal force, on a substantially similar area of the vaginal walls, when measuring a width of the vagina. Such measurement emulates closely the effect on the vagina walls which will be caused by a fitted pessary.

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Although the present invention describes a device for measuring a vagina for fitting a pessary to the vagina, it should be understood that other hollow orifices within the human body may be measured in the same way, or based on the principles described within, and pessaries and/or similar devices fitted accordingly.

In the following detailed description, numerous specific details are set forth in order to provide a thorough understanding of the present invention. However, it will be understood by those skilled in the art that the present invention may be practiced without these specific details.

For purposes of better understanding some embodiments of the present invention, as illustrated in FIGS. 1G, 2A-2F, 3A-3B, 4, 5A-5C, 6A-6D, 7A-7C, 8A-8D, 9A-9E, 10A, 10B, 11A, and 11B of the drawings, reference is first made to FIG. 1A, which is a simplified illustration of one example of a pessary in place in a vagina.

FIG. 1A depicts one type of a pessary 200, in place in a woman's body, with some nearby organs also depicted. It is noted that pessaries come in different shapes and sizes. Different shapes of pessaries are intended to correspond to different uses intended for the pessaries. Different shapes of pessaries include pessaries with a different number of "arms" and/or knobs, sizes of knobs, shapes of knobs, hollow rings, solid rings, rings with holes, and so on. Different sizes for the pessaries are dependent of sizes of the patient's vagina, and optionally on the amount of force which part of the pessary is intended to apply against the vagina wall.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

The word "pessary" as used herein may encompass a device, or an appliance of varied form, introduced into the vagina.

The pessary may be intended, by way of some non-limiting examples, to support the uterus and/or to correct a displacement of a vaginal wall; a medicated vaginal suppository; or any of various devices worn in the vagina to support and/or correct the position of the uterus or bladder or the rectum, or to prevent or to minimize pelvic organ prolapse, and/or assist in preventing urinary incontinence.

Figure 1B:
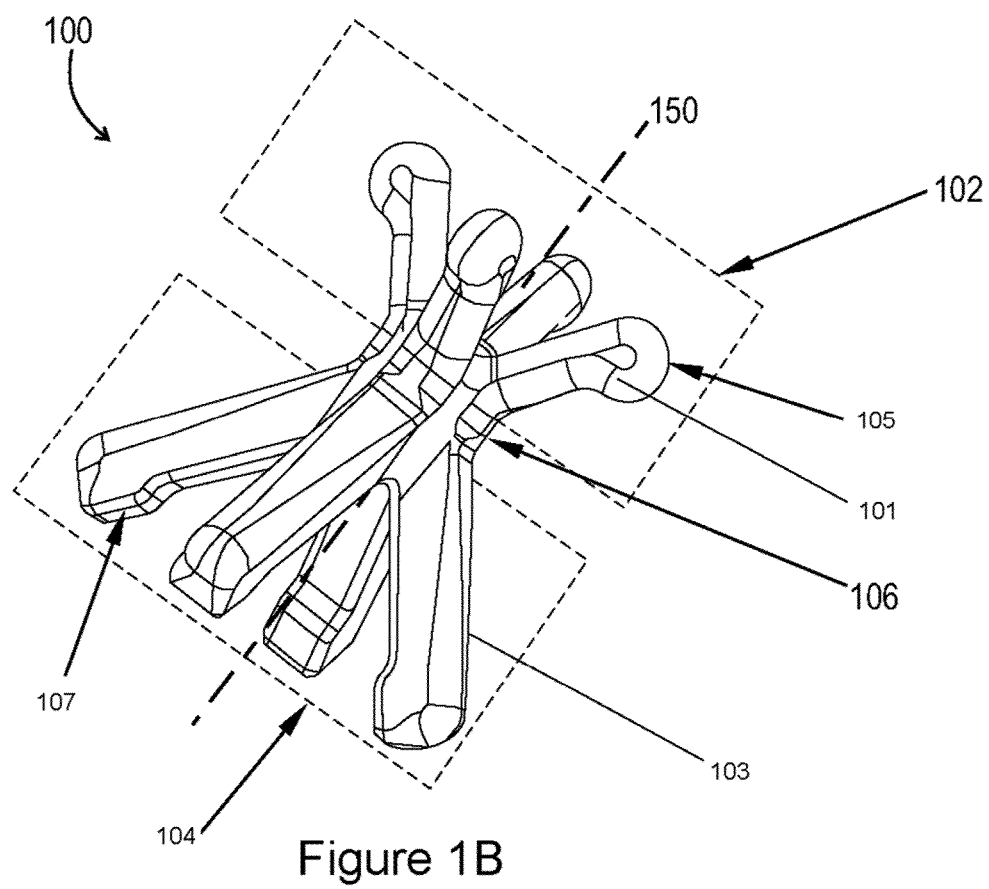
FIG. 1B is a simplified illustration of an example of a Pessary for treating urinary incontinence.

Reference is now made to FIG. 1B, which is a simplified illustration of an example of a Pessary for treating urinary incontinence. The device 100 depicted in FIG. 1B is a pessary for treating urinary incontinence constructed according to an exemplary embodiment of a device for treating urinary incontinence as described in commonly-owned U.S. Provisional Application No. 61/263,854.

The description of FIG. 1B is substantially taken from the above-mentioned patent application, in order to explain how fitting a pessary optionally involves measurements at different depths within the vagina, optionally at specific directions which optionally correspond to arms, or knobs, protruding from a pessary center axis, and optionally include measuring forces applied on walls of the vagina at locations which the arms will contact the vagina walls.

It is noted that the device 100 of FIG. 1B is constructed of a flexible material, and acts as a spring, bending flexibly and applying force on the vaginal walls.

Referring to FIG. 1B, a perspective view of an exemplary embodiment of the device 100 is shown. For ease of description, the device 100 is arranged around a central axis 150 and divided into three basic elements. A top section 102, inside the dashed box, is provided which serves as the "anchoring" element, for stabilizing the device 100 within the vagina. There are at least three types of anchoring, axial anchoring which acts in the direction along the central axis of the vagina, and radial anchoring which acts side-to-side or substantially perpendicular to the central axis of the vagina and/or rotational anchoring, described in more detail below. A bottom section 104 is provided which serves as the "supporting"

element, for generating support. In some embodiments of the invention, the roles of the anchoring and supporting elements could be switched or shared. In some embodiments of the invention, support is generated at a sub-urethral location, for example mid-urethra. Alternatively, additionally and/or optionally, support is generated at the bladder neck. In some embodiments of the invention, the bottom supporting section 104 provides at least one form of anchoring described above to help anchor device 100 in position.

Also, an intermediate section 106 is optionally provided which acts as a "node" and which connects anchoring 102 and supporting 104 sections. The node 106 of device 100 has a length which is only a small portion of the overall length of the device, in some embodiments of the invention. In some embodiments of the invention, the length of the node is less than 15% of the entire length of the device. In some embodiments of the invention, the length of the node is less than 20% of the entire length of the device. In other embodiments of the invention, the length of the node is less than 30% the entire length of the device. In some embodiments of the invention, a node which is short relative to the entire length of the device relative to a same length device with a long node, allows for more flexibility in varying the stiffness, the comfort, and the size of device 100.

In an exemplary embodiment, the anchoring element 102 and the supporting element 104 have four (4) arms 101 and 103, respectively. Optionally, these elements have more or less arms. In an exemplary embodiment of the invention, four arms are provided to each section in which two generally exert pressure towards the anterior vaginal wall, and two generally exert pressure towards the posterior vaginal wall adjacent the bowels. The distal part of the urethra extends into the vagina, forming a recess between the urethral bulge and the vaginal wall. The two support arms which exert pressure anteriorly fit within these natural recesses on either side of the urethra, in some embodiments of the invention. Optionally, the anchoring and supporting elements are provided with more or less arms. For example, the anchoring element could have more arms if there is concern about unwanted movement of device 100. In an exemplary embodiment of the invention, the anchoring element 102 does not apply significant pressure to the wearer's vagina and/or urethra, thereby enhancing comfort. It should also be noted that for certain women, the described devices herein can also be used as a treatment or part of a treatment for prolapse.

Anchoring arms 101 of the device 100 prevent the device 100 from moving unintentionally out of position. In some embodiments of the invention, the supporting arms 103 contribute to at least one of the three types of anchoring described above, for example rotational anchoring. In an exemplary embodiment of the invention, the arms 101 are flexible and/or elastic and/or resilient. This flexibility enhances the anchoring arms' 101 ability to prevent motion of the device 100 further into the vagina. As force strives to exert itself on the device 100, and move it further into the vagina, the flexible anchoring arms 101 tend to spread apart. This spreading action of the anchoring arms 101 increases the friction between device 100 and the vaginal wall, preventing movement. While the arms 101 are flexible, it should be noted that they are rigid enough and/or are configured to spread to prevent unwanted motion of the device 100 towards the entrance of the vagina. Optionally, the arms 101 are rigid but the node is flexible, the node thus providing flexible anchoring and support.

Movement towards the vaginal opening is resisted by the support arms 103 which tend to widen radially when pulled outwardly. These features work with the tenting behavior of the vaginal walls described above, which also helps to maintain the device 100 in place, as described in more detail below.

In an embodiment of the invention, anchoring arms 101 are shorter than supporting arms 103, as shown in FIG. 1B. In an embodiment of the invention, anchoring arms 101 are a consistent size in a line of different products of device 100 (such as described below) even though the supporting arms 103 may vary in size and/or performance. Anchoring arms 101 are the same size, in some embodiments of the invention, to ease manufacturing considerations. Optionally, the anchoring arms 101 and supporting arms 103 are the same size. In some embodiments of the invention, tips 105 of anchoring arms 101 are rounded or spherical in nature, to provide smooth surfaces (i.e. no corners or points) for the tenting of the vaginal wall.

An additional optional feature of the anchoring arms 101 of the device 100 is that they operate remotely, relative to the longitudinal axis of the vagina, from the support arms 103.

In an exemplary embodiment of the invention, the tips 107 of supporting arms 103 and/or corners of device 100 are blunted by a beveled edge both along the arms 101, 103 and at the tips 107. Optionally, tips 107 are slightly rounded and/or have a beveled edge. In an embodiment of the invention, the beveled edge of the supporting arms 103 reduces the overall circumference of the device, relative to a completely spherical cross section, when it is in a compressed mode for packaging within an applicator.

Figure 1C:
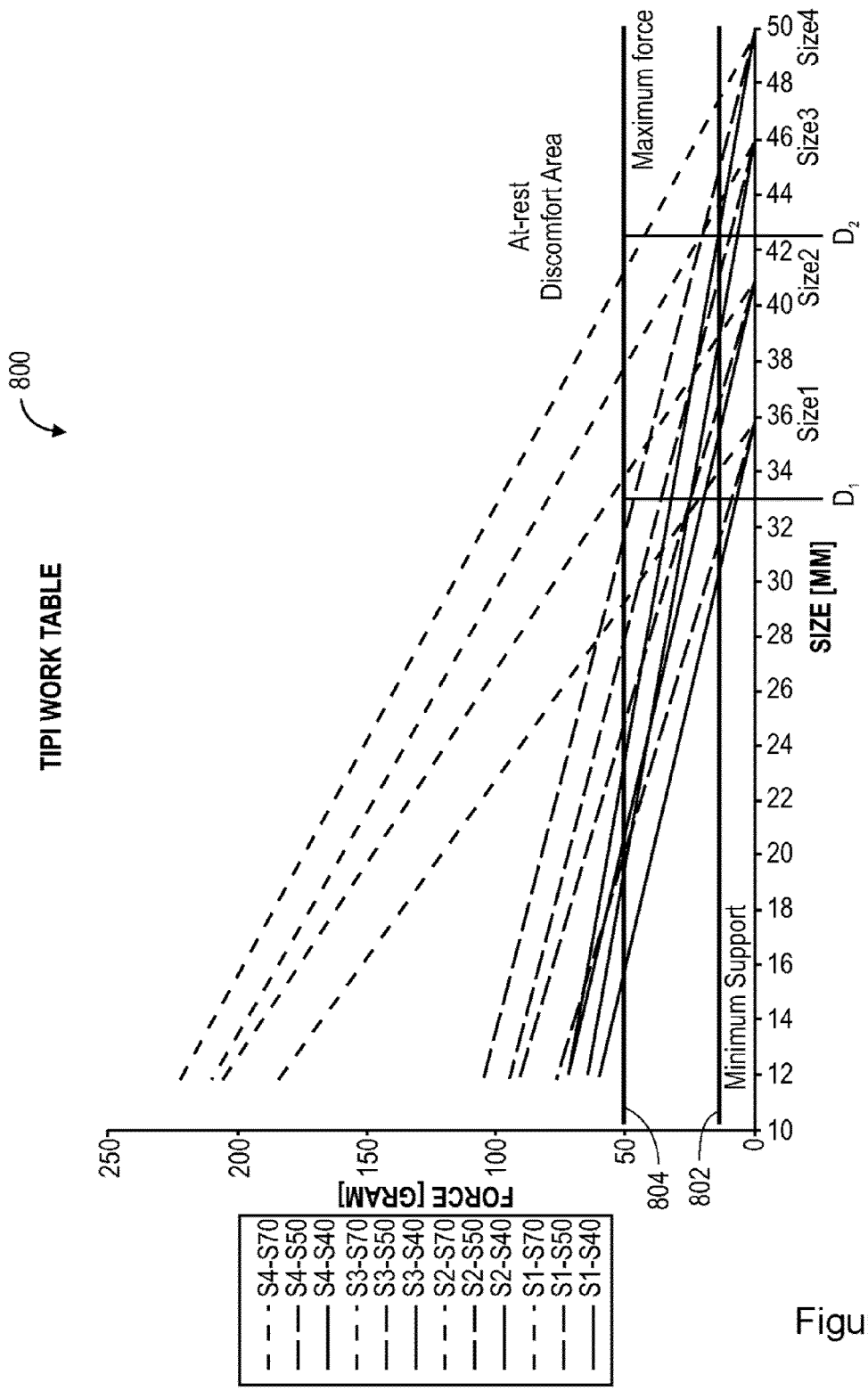
FIG. 1C is a device performance graph correlating force exerted to Pessary size and diameter and hardness, for the example Pessary of FIG. 1B.

Reference is now additionally made to FIG. 1C, which is a device performance graph correlating force exerted to Pessary size and diameter and hardness, for the example Pessary of FIG. 1B;

The device performance graph depicted in FIG. 1C is for the pessary for treating urinary incontinence of FIG. 1B.

The description of FIG. 1C is substantially taken from the above-mentioned patent application, with the same rationale as listed above with reference to the description of FIG. 1B.

FIG. 1C is a device performance graph 800 correlating expansive force exerted by support arms 103 (y-axis) to amount of medial deflection (x-axis) and hardness (line hatchings) for each of four basic configurations shown in of the device 100, in accordance with an exemplary embodiment of the device 100, and whereby medial deflection is the distance in mm towards the central longitudinal axis of the device from the natural expanded state of the arm.

The expansive force exerted by the supporting arms 103 is generally determined by the hardness grade and/or the medial flexion degree (medial deflection) of each of the supporting arms 103 relative to the central axis 150, in an embodiment of the invention. As described in other related applications (e.g. FIG. 5 of PCT/IL2006/000346), in some embodiments of the invention, an internal structure is included to assist with determining the medial deflection of each of the arms. If a specific material is used in construction, for example liquid silicone, these forces can be measured for any given diameter of the arms 103 of device 100, knowing the performance characteristics of the specific material being used. Using this data in a graph where the x-axis represents the device diameter and the y-axis represents the force, the forces exerted by the arms for a given device size and its material hardness grade is demonstrated, in an exemplary embodiment of the invention. The slope represents the ratio between the force (grams) and the amount of medial deflection (mm), in an embodiment of the invention.

In designing and/or selecting device 100 for use, certain performance considerations may be taken into account. It should be noted that device 100 support is "activated" by the supporting arms 103 being compressed at least slightly by the vaginal wall. In general, the stronger the compressive forces on the supporting arms 103, the stronger the support force that is exerted back onto the vaginal wall/sub-urethra by the supporting arms 103. For example, supporting arms 103 must be compressed a certain minimal amount in order to provide counterforce sufficient for the supporting arms 103 to render support. That is, if a device 100 is inserted into a vagina and the device is too small or the angle of radial expansion is too small, then not enough force will be applied to the support arms 103 from the vaginal wall to cause the support arms 103 to counter with the force required to render appropriate and effective support. Failure to achieve this minimal value of compression in an at-rest state, shown as a horizontal minimal applied force line 802 in FIG. 1C, on the supporting arms 103 during a stressful event will reduce device efficacy, in an embodiment of the invention. It should be noted that in some embodiments of the invention, the minimal applied force line 802 at 10 g is approximate and/or is variable ±3 grams.

Similarly, there exists is a maximum force exerted by the device on the vaginal walls beyond which the user would experience discomfort while the device is in the vagina at-rest and/or while removing the device, therefore in an embodiment of the invention, device 100 is designed and/or selected for use not to exceed this maximal force. This maximal force is represented in FIG. 1C as the bold horizontal line 804 at approximately 50 g of force. In an embodiment of the device 50 grams is approximate and can vary ±5 grams. For example, if the radial expansion of the supporting arms 103 is too great, it will generate excessive force on the vaginal wall, the user may experience discomfort, which is to be avoided in an embodiment of the invention.

The graph 800 is used in an embodiment of the device 100, to determine the use potential for a specific device configuration for a specific vaginal size. For example, D1 on graph 800 represents a vagina with a diameter of 33 mm. Referring to graph 800, it can be seen that Size 1 devices at S40 and S50 are not indicated for use with this patient because they will not provide sufficiently effective support in an at-rest state. However, a number of other device configurations are considered acceptable:
1. Use size 1 of shore 70 device (supplying force of ~21 g)
2. Use size 2 of shore 50 device (supplying force of ~25 g)
3. Use size 2 of shore 40 device (supplying force of ~20 g)
4. Use size 3 of shore 50 device (supplying force of ~38 g)
5. Use size 3 of shore 40 device (supplying force of ~28 g)
6. Use size 4 of shore 50 device (supplying force of ~48 g)
7. Use size 4 of shore 40 device (supplying force of ~35 g)

As another example, D2 on the graph 800 represents a vagina with a diameter of 42.5 mm. Because of the size of this patient's vagina, fewer choices are available to her for receiving ideally efficacious vaginal support. In this example, likely choices would include:
1. Use size 3 of shore 70 device (supplying force of ~22 g)
2. Use size 4 of shore 70 device (supplying force of ~45 g)
3. Use size 4 of shore 50 device (supplying force of ~22 g)
4. Use size 4 of shore 40 device (supplying force of ~18 g)

It is noted that a size 4 device made of a low Shore hardness material, for example 40, can be used for a wide variety of vaginal diameters (approx. 30 mm to 45 mm), in an exemplary embodiment of the invention.

Above the maximal force line 804, graph 800 shows force exertion levels of the various device configurations at different levels of medial deflection all the way down to about 12 mm in total device diameter. In an embodiment of the invention, each arm is approximately 6 mm in width, therefore the minimum diameter distance possible is when two opposing arms have come into contact or 12 mm (6 mm+6 mm).

The term "Pessary Caliber", or "PC", as used herein, is intended to encompass apparatuses, systems, appliances, and/or devices for measuring and/or fitting a pessary device for a patient or user.

Fitting and decision regarding the correct size of the pessary is a major issue in the likelihood of patients to use a pessary. At present, there is no known systematic way to initially decide upon the correct size of the pessary. The doctor typically estimates a size, the patient buys a pessary and a trial fitting is begun. The patient is sent home with the pessary in situ. If she is happy with the pessary, fitting is completed. If the device falls out or applies too much pressure, or causes difficulties with voiding or defecation, then another size should be tried, at additional costs. Sometimes, this necessitates 1-3 additional rounds of fittings; hence compliance to treatment is reduced. In order for a pessary to fulfill its intended use, it should have the proper or correct size for the particular vagina in which it is to be used, and there should be sufficient perineal body in order to retain the pessary within the vagina.

A well fitted pessary optionally fulfills one or more of the following characteristics:

The pessary is well placed and will not fall out of the vagina, preferably not even during strenuous movement, lifting, and so on. An example test for "not falling" is a "sneeze test" or a "cough test", that is, the woman sneezes or coughs with the pessary in place, and checks whether the pessary slips out of place.

The pessary exerts pressure against the vaginal wall. While too little pressure may not provide the support which the pessary is intended to provide, too much pressure may injure the vaginal wall, and/or may become so uncomfortable, and possibly painful, the patient will not be willing to put up with wearing the pessary for long.

According to some embodiments of the present invention, a Pessary Caliber, hereinafter referred to as PC, is herein provided, which can facilitate fitting or measurement. Advantages provided by of some embodiments of the PC include: a comfortable and painless method to assess the feminine pelvic floor; a device to gain data regarding Vaginal width and/or Vaginal depth, and/or force exerted on vaginal walls by pushing the walls to the measured width; and data regarding the above dimensions and the presence of sufficient perineum to retain the pessary.

Reference is now made to FIGS. 1D-1F, which are simplified illustrations of an example of a Pessary 300 for treating pelvic organ prolapse, constructed according to an exemplary embodiment of a device for treating urinary incontinence as described in commonly-owned Published PCT Patent Application Number WO2009/130702.

The descriptions of FIGS. 1D-1F are substantially taken from the above-mentioned patent application, in order to explain how fitting a pessary optionally involves measurements at a specific depth within the vagina, optionally at specific directions which optionally correspond to where a circumference of the pessary will contact the vaginal walls, and optionally include measuring forces applied on walls of the vagina at locations which the arms will contact the vaginal walls.

Exemplary Support Mechanism

In some embodiments of the invention, a support mechanism 309, alternatively referred to as locking mechanism 309, comprises two arms 306 that are rotatably connected at hinge 314, alternately referred to as rotation axis 314. Optionally a string 318 is attached to the rotatable connection that serves to unlock arms 306, as will be explained below. Arms 306 are attached to limiters 310 along ring 302 with peripheral hinges 312.

Figure 2:
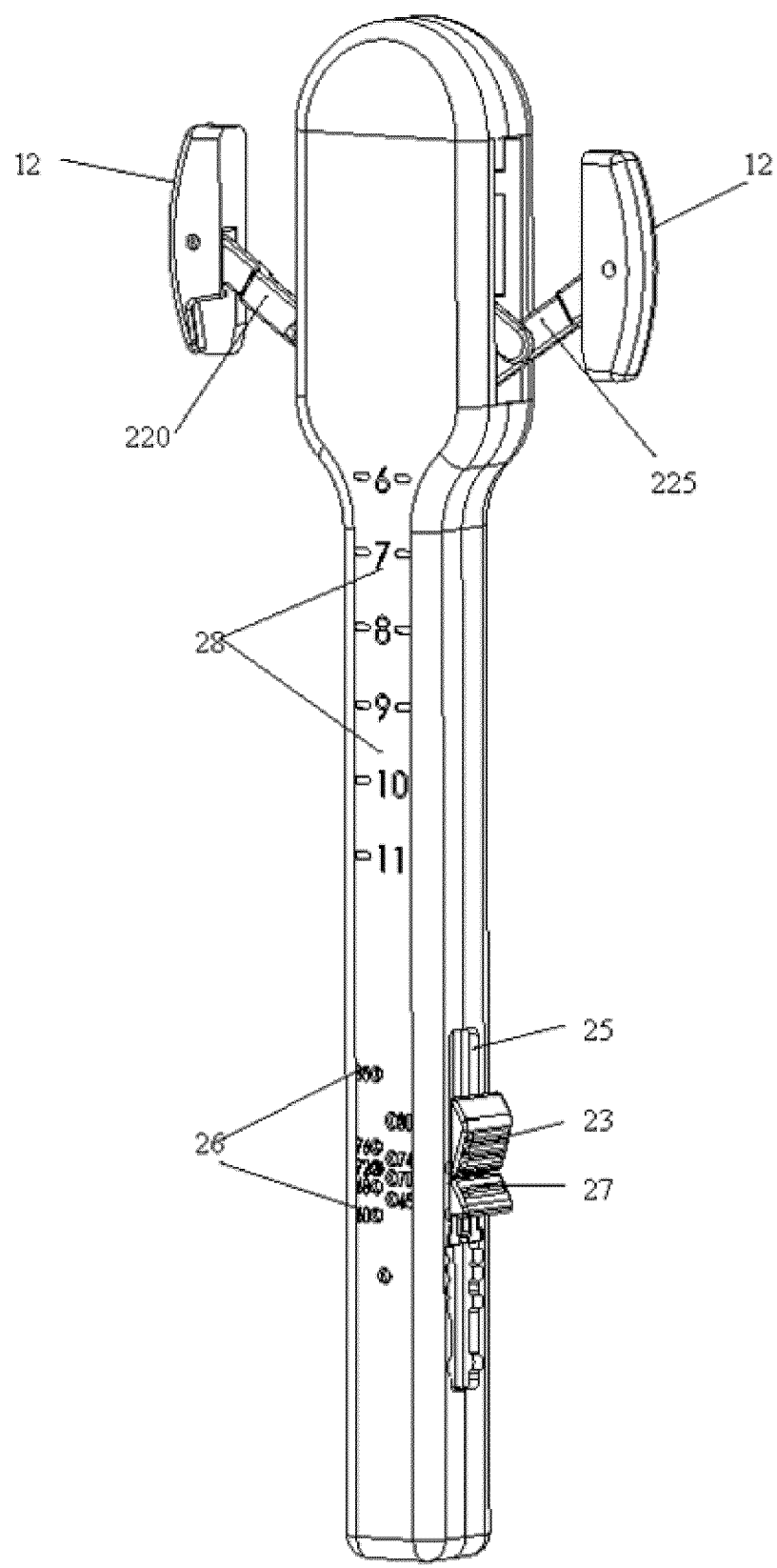
FIGS. 2A-2F are simplified illustrations of a PC device, according to some embodiments.
Figures 2B, 2C:
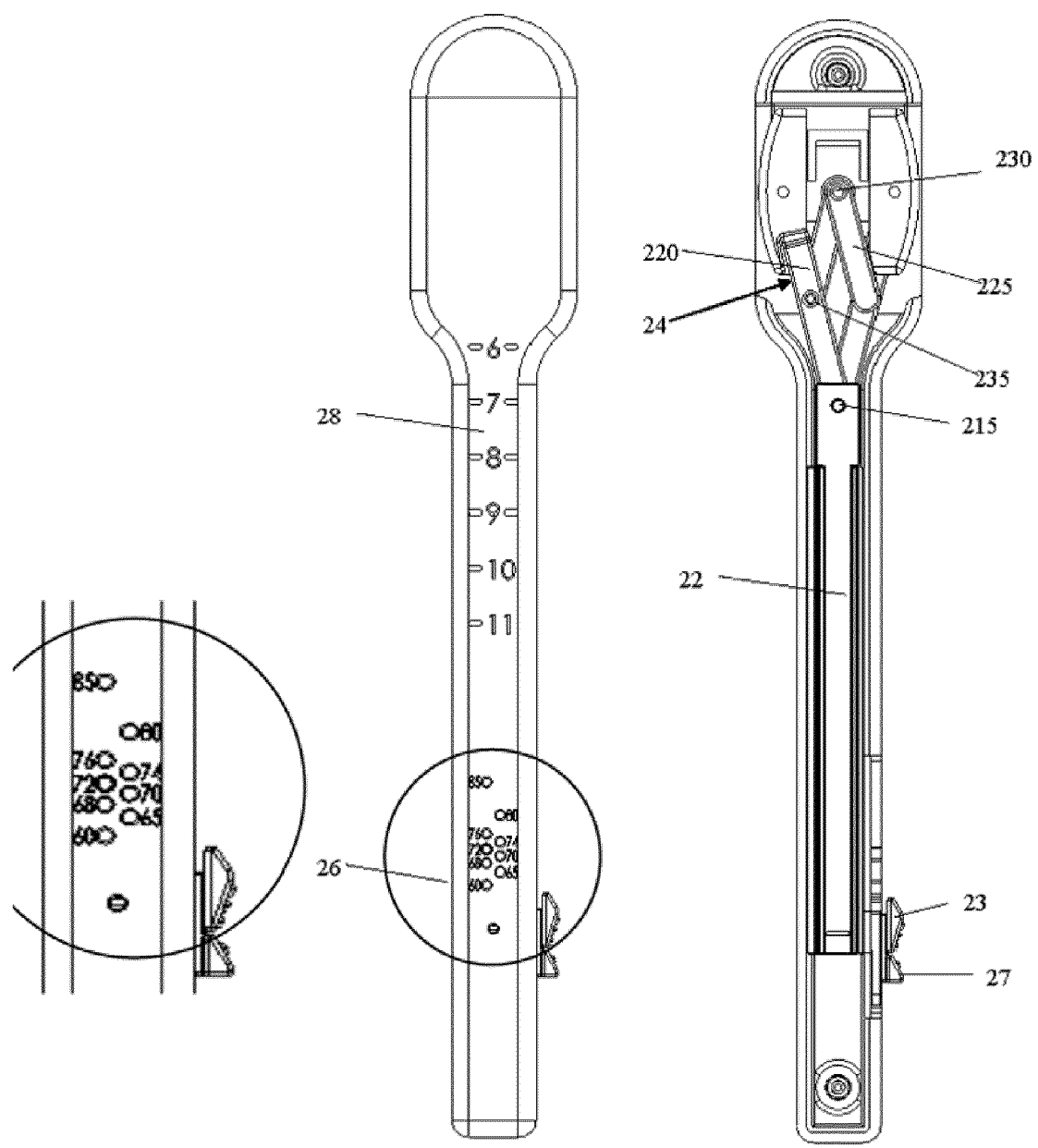

Initially, ring 302, in the compact configuration, is inserted into a vagina 311 with arms 306 folded. During deployment, hinge 314 is pressed in a direction 319 to cause ring 302 to expand while arms 306 unfold (FIG. 2B). Ring 302 achieves a maximally expanded configuration (FIG. 2C) in which support curves 301 and 303 press laterally against the tissue of opposite and lateral aspects of vagina 311.

In the expanded configuration, limiter edges 322 press against arms 306, and lock arms 306 to maintain support mechanism 302 as a span across ring 302 while forming an angle having an apex above a transverse line k-k.

Exemplary Prolapse Alleviation

Without necessarily precluding other methods of use, the following exemplary method is provided, which may affect size, resilience and/or exact shape of the device. While laterally pressing the tissue of vagina 311, noted above, support curves 301 and 303 cause the tissue of vagina 311 to stiffen. The lateral pressure from support curves 301 and 303 causes flattening and stretching of anterior and posterior walls of vagina 311, so that a prolapsed apex of vagina 311 is stretched upward.

Additionally or alternatively, flattening and stretching of anterior and posterior walls of vagina 311 reduces prolapse associated with one or more external organs comprising the bladder, rectum, small intestine, and/or uterus.

Alternatively or additionally, the pessary optionally includes a membrane or cross-element which directly supports organs.

A device performance graph correlating force exerted to Pessary size and diameter and hardness may be developed for the pessary of FIGS. 1D-1F as well.

Figure 1G:
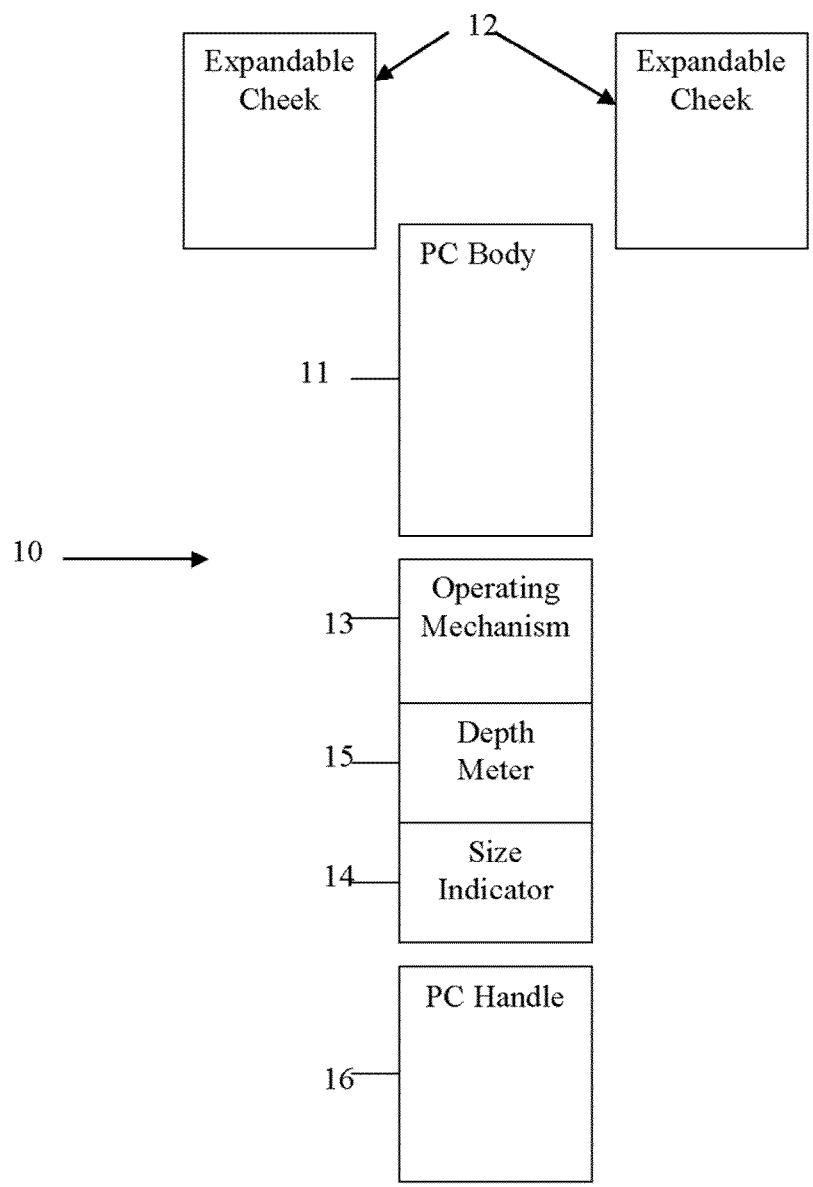
FIG. 1G is a simplified block diagram of some Pessary Caliber (PC) device components, according to some embodiments.

Reference is now made to FIG. 1G, which is a simplified block diagram of some Pessary Caliber (PC) device components, according to some embodiments.

As can be seen in FIG. 1G, the system may include one or more of the following five distinct parts: A body 11 of the device; handle or grip 16; two or more expandable "jaws", "arms" or "cheeks" 12 for measurement of vaginal and perineal dimensions, thereby indicating pessary size; an operating mechanism 13 which is responsible for expanding and collapsing the "cheeks" 12; a size indicator 14; and a depth meter 15. The body and the contour of the device 10 may have various structures. One such structure is described herein as having a wider part for an opening mechanism and a slim part acting as a handle, but it should be emphasized that many shapes, materials, textures and forms may be used.

It is noted that the order in which the operating mechanism 13, the size indicator 14; and the depth meter 15 are depicted in FIG. 1G is not intended to imply a necessary order of construction in all embodiments of the invention.

Reference is now made to FIGS. 2A-2F, which are simplified illustrations of a PC device, according to some embodiments.

FIGS. 2A-2F illustrate components of the PC device, and an embodiment of a control mechanism for controlling PC cheek expansion.

As can be seen in FIGS. 2A-2F, a rod 22 links between a knob 23 and a cheek opening mechanism 24. Sliding the knob 23 within a slot 25 pushes the rod 22 up and down within the body, and the handle of the PC. The rod 22 is connected rotatably via a connection 215 to arms 220 which are supported by supports 225 and a connection point 230. The arms 220 and the support 225 connect at an axle 235. An axle 230 is fixed to the body of the PC, hence a longitudinal movement of rod 22 along the body and handle of the PC forces the arms 220 to extend outwards, pushing the cheeks 12 laterally. The reach or distance moved by the cheeks 12 may be shown within windows 26, or by other suitable measurement indicators. The reach indicates, for example, vaginal cavity width or size. Further, additional cavity or anatomy measurements may be viewed in accordance with numbers 28, which, for example, may indicate vaginal cavity depth, according to how far the PC is inserted into the vagina.

In some embodiments, the knob 23 may be kept in a desired position while measurement is being read by a practitioner or user, by using a locking knob 27 to optionally substantially prevent movement of the knob 23. For example, the knob 27 may be a mechanical locking mechanism for locking or unlocking the position of knob 23. In one example a ratchet type mechanism, similar to that of a utility knife (also called a box cutter, a boxcutter, a razor blade knife, a carpet knife, a Stanley knife, snap knife or a stationery knife) may be used, or other relevant mechanisms.

Figure 2D:
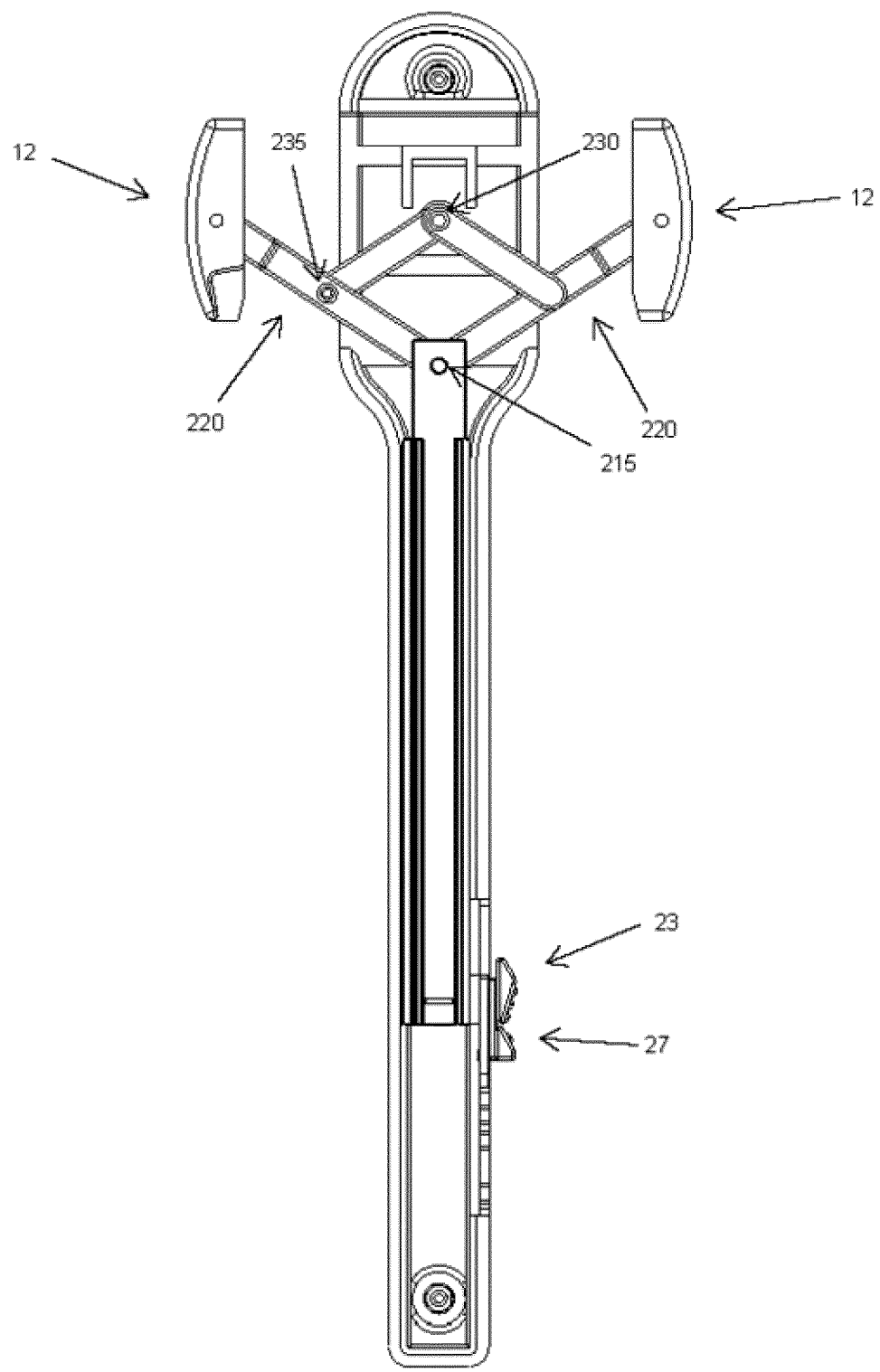
Figure 2E:
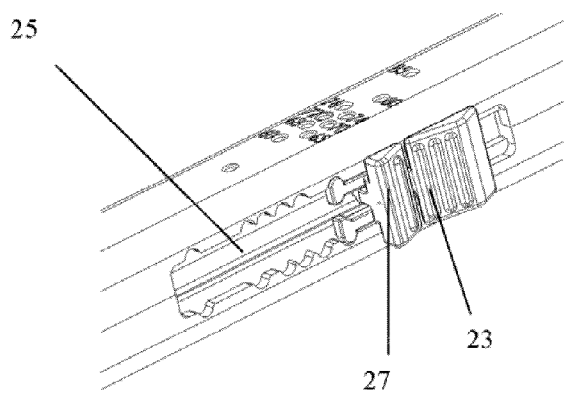
Figure 2F:
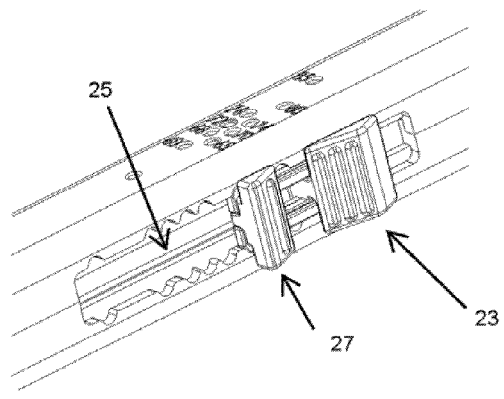

FIGS. 2A-2F show numerous views and examples of PC device control mechanism configurations. For example, FIG. 2F shows the locking mechanism in a closed or locked state, and FIG. 2E shows the locking mechanism in an open or unlocked state. FIGS. 2B and 2C show the PC device in a compact pre-deployed state, while FIG. 2D shows the PC device in its deployed state, in which the cheeks are opened laterally, as needed.

Some typical dimensions of example embodiments of the present invention are now described.

The PC device, at least in the part to be inserted into a vagina, has a cross section small enough be inserted into a vagina. The cross section of the portion which is inserted into the vagina, of the device of FIGS. 2A-2F, is a round-cornered rectangular shape of approximately 25 mm by 15 mm, when the cheeks are not extended. The cheeks are extendable to a width of approximately 95 mm. The length of the portion which is inserted into the vagina is approximately 110 mm. The total length of the device of FIGS. 2A-2F is approximately 20-22 cm.

In the device of FIGS. 2A-2F, the cheeks are approximately 30 mm in length, and approximately 5-6 mm in width. A radius of curvature of the cheeks, on the side which presses against the vaginal walls, is substantially similar to the radius of curvature of the pessary arm tip which presses against the vaginal walls.

Figure 3B:
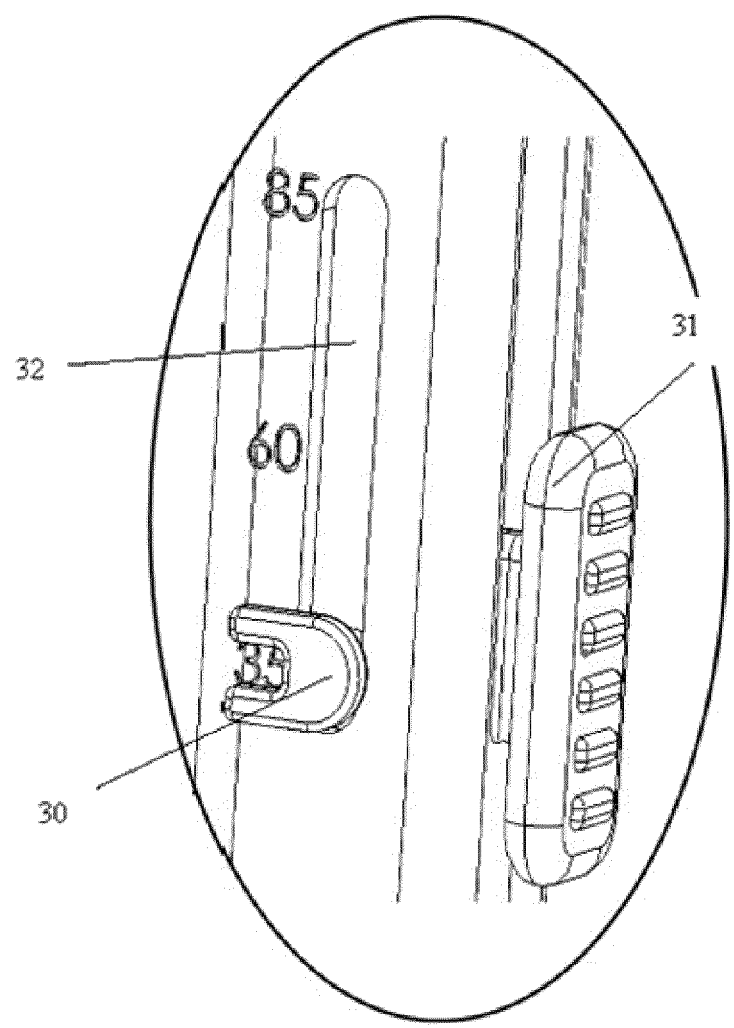
FIGS. 3A-3B are simplified illustrations of an alternative embodiment of a PC device.
Figure 3A:
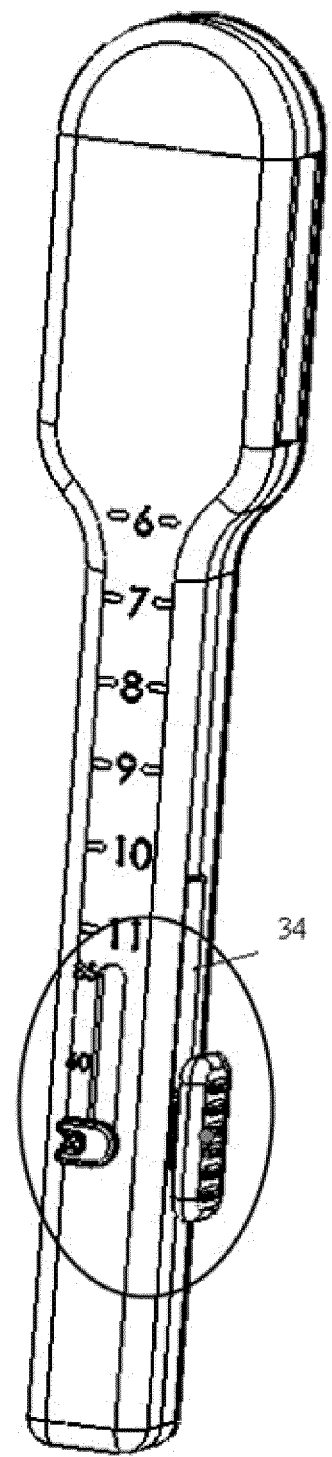

Reference is now made to FIGS. 3A-3B, which are simplified illustrations of an alternative embodiment of a PC device. The embodiment of FIGS. 3A-3B depicts a different operating mechanism and different depth and size indicators than described with reference to FIG. 2A-2F.

In some embodiments, the shape of faces of the cheeks 12 which are designed for pressing against the vaginal walls are shaped substantially similarly to the shape of a portion of a pessary which abuts against the vaginal wall, such as the curvature of the pessary of FIGS. 1D-1F, or the tips 105 107 of the arms 101 103 depicted in FIG. 1B. This measurement of size and shape of the vagina correspond to the size and shape "felt out" by the pessaries which are being fitted.

FIGS. 3A-3B depict a measurement indicator 30 for indicating a correct pessary size, corresponding to a distance between the cheeks, by moving within a first slot 32.

A cheek control mechanism 31 is slid within a second slot 34, according to one embodiment. As with the other examples shown herein, the distances shown by indicator 30 are optionally coded or calculated to represent the distance of the extension of the cheeks, and/or a pessary size.

Figure 4:
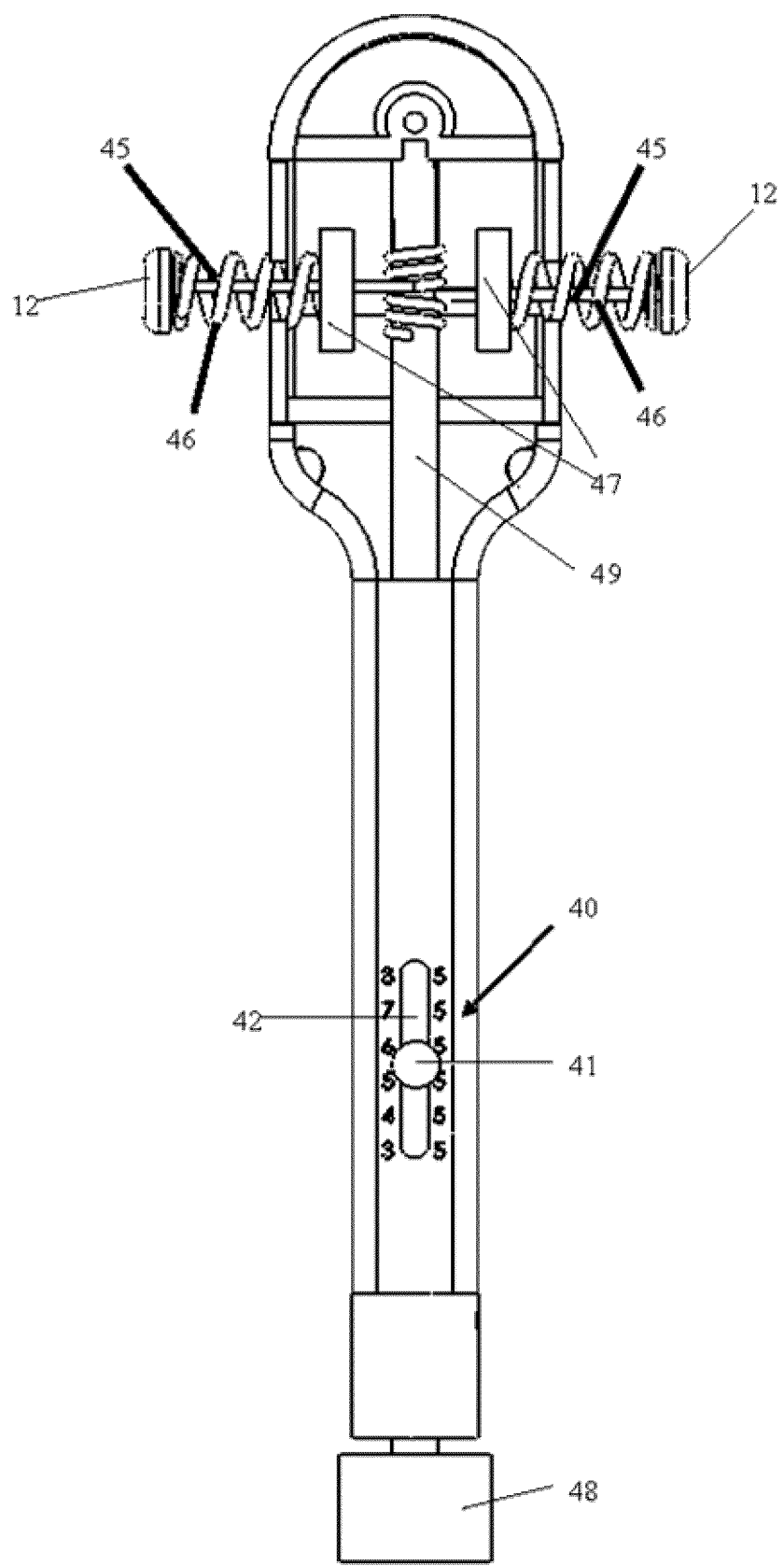
FIG. 4 is a simplified illustration of another alternative embodiment of a PC device.

Reference is now made to FIG. 4, which is a simplified illustration of another alternative embodiment of a PC device. FIG. 4 depicts a measurement indicator 40 for indicating a pessary size by sliding a cheek control mechanism 41 within a slot 42, and an alternative cheek operation mechanism in an alternative embodiment of the present invention.

The cheeks 12, which appear small in FIG. 4, and may have a larger surface area where required, may be pre-tensioned with a wire 45 within a spring 46. A turning knob 48 turns a rod 49 right or left according to needs. During a pre-deployed state, the cheeks 12 are located within the PC close to bars 47. Optionally turning the knob 48 will unwrap the wire 45, and allow the spring 46 to push the cheeks 12 laterally. Turning the knob 48 in a counter direction will cause wrapping of the wire 45 on the rod 49, hence tightening the wire 45 and causing retraction of the cheeks 12 back into an optional recess in the PC. In some embodiments of the invention, the rod 49 may optionally be held in position by a friction mechanism or a one way movement mechanism such as an optional ratchet. A press on a release button (not shown) optionally allows the rod 49 to rotate, acting due to the tension within the spring 46.

Figure 5C:
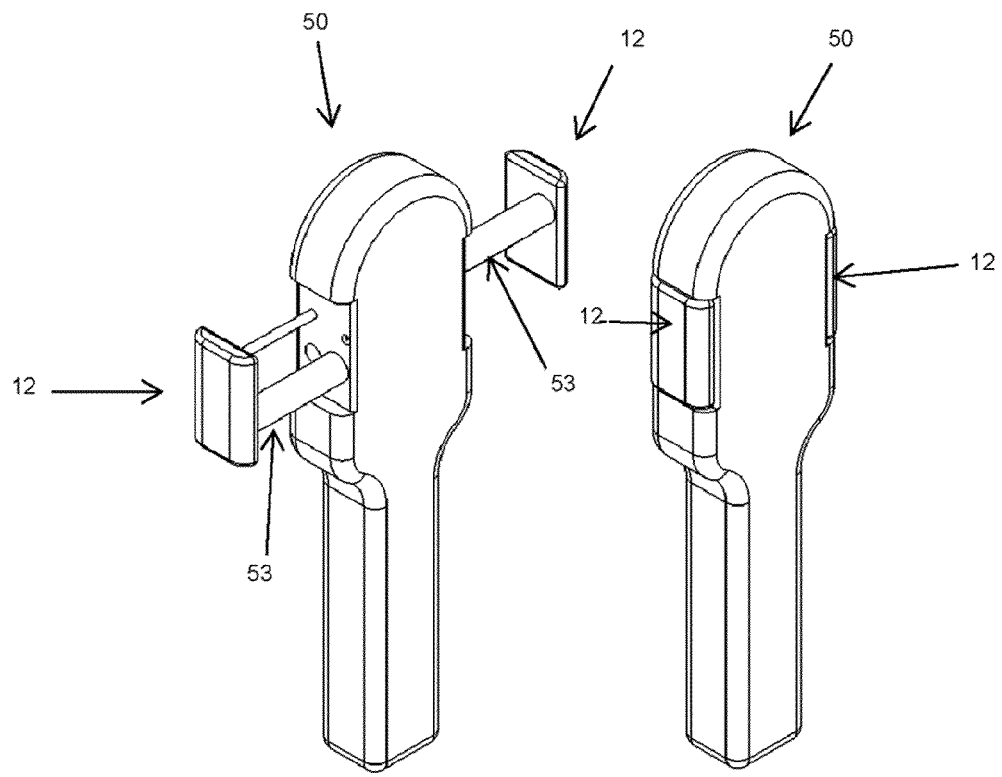
Figure 5C:
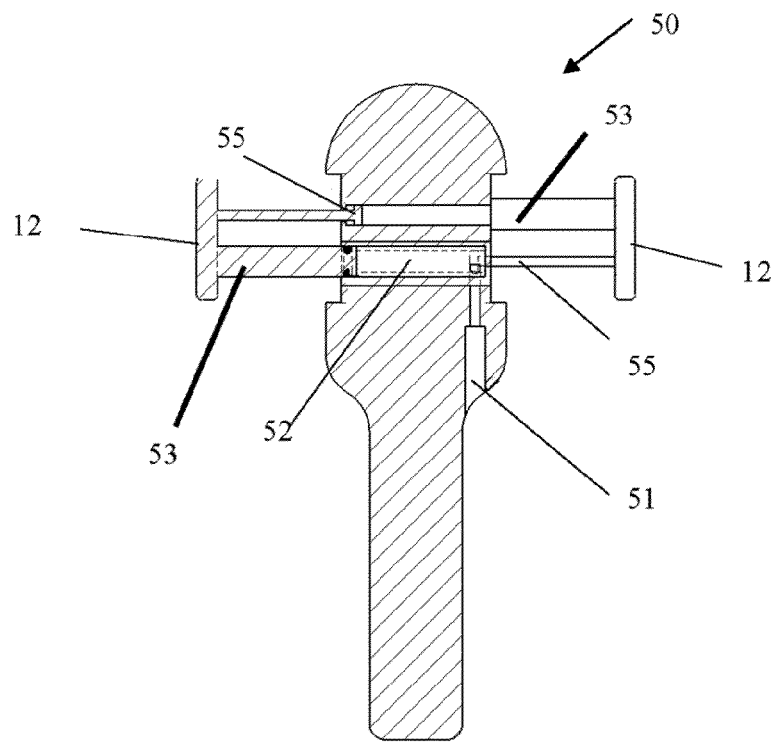
Figure 6A:
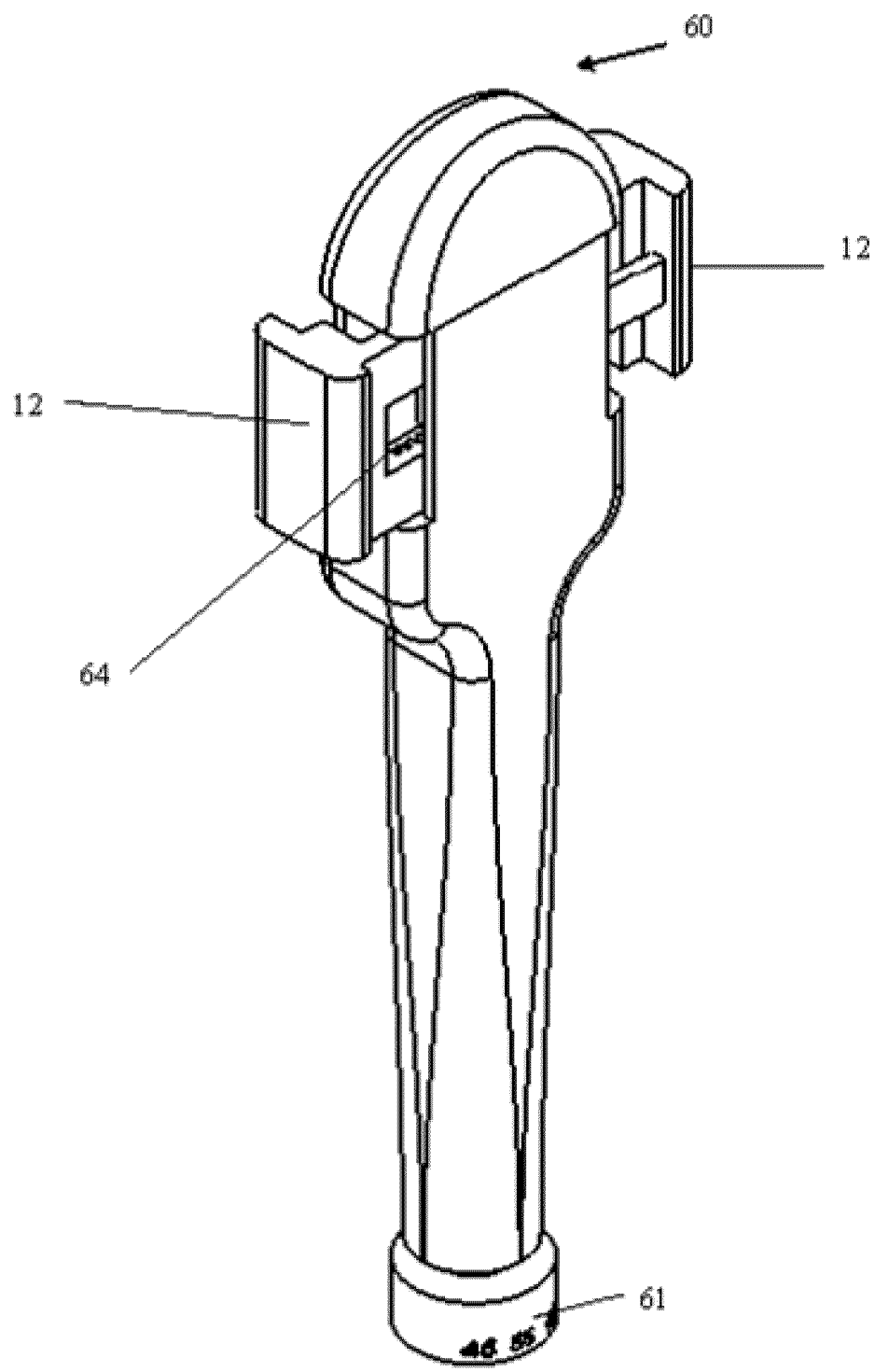

Reference is now made to FIGS. 5A-5C, which are simplified illustrations of yet another alternative embodiment of a PC device. FIGS. 5A-5C, depict a pneumatic cheek control mechanism 50 for enabling measurement of a vagina.

As can be seen in FIGS. 5A-5C, the mechanism 50 optionally enables gas (pneumatic mechanism) or liquid (hydraulic mechanism) to be pumped or pushed through a tube 51, optionally from an external source such as a syringe, into a chamber 52, in which pistons 53 are pushed laterally as a function of the gained pressure, thereby pushing cheeks 12 externally. In some embodiments, measurement of the extension of the cheeks may be indicated on a measurement indicator on the body of the PC.

In other embodiments measurements may be determined according to the volume of gas or liquid pushed into the chamber 52. Such a volume may be indicated on a measurement indicator on the body of the external source, such as a syringe, and/or on an indicator coupled to the tube 51.

In some embodiments, when using liquid, the measurement of the amount of liquid pushed into the chamber 52 is optionally substantially exact, and correlates directly to a distance which the cheeks 12 extend. In such embodiments a force by which the cheeks press against the vagina is optionally measured, optionally by measuring the pressure of the liquid.

In some embodiments, when using gas, or a mixture of gases such as air, the distance which the cheeks 12 extend correlates to a measurement of the amount of gas pushed into the chamber 52, taking into account a pressure of the gas in the chamber 52. The force by which the cheeks press against the vagina is also optionally measured, optionally by measuring the pressure of the gas.

In some embodiments, the force is measured by using a result of measuring the pressure of the gas or the liquid. In some embodiments, force of the cheeks against the vaginal wall is measured. In some embodiments, the force is measured by using a result of measuring with a pressure transducer. In some embodiments, pressure transducers are placed on the cheeks, and the force by which the cheeks press against the vaginal wall is calculated based on measurement by the pressure transducers.

In some embodiments, the maximum force exerted through the cheeks is settable, optionally be setting a limit to pressure, in cases of gas or liquid extension of the cheeks, or a limit to torque, in cases of a mechanical extension of the cheeks.

In some embodiments, the shape of faces of the cheeks 12 which are designed for pressing against the vaginal walls are shaped substantially similarly to the shape of the pessary which pushes against the vaginal walls, such as, by way of a non-limiting example, the curvature of the example pessary of FIGS. 1D-1F, or the tips 105 107 of the arms 101 103 depicted in FIG. 1B.

This measurement of size and shape of the vagina, and pressure applied to walls of the vagina, correspond to the size, shape, and force, "felt out" by the pessaries which are being fitted.

In some embodiments, the PC optionally has cheeks 12 with a cross sectional area substantially equal to the cross sectional area of a portion of the pessary which abuts the vaginal walls, such as, by way of a non-limiting example, the example pessary of FIGS. 1D-1F, or the tips 105 107 of the arms 101 103 depicted in FIG. 1B. Using a substantially equal cross sectional area produces a situation wherein the pressure applied by the cheeks is the same as applied by the arms, when the force applied by the cheeks is the same as applied by the arms.

Using a substantially equal cross sectional area also prevents damage to the vagina walls. The PC does not press on the walls hard enough to damage, since the PC does not press any harder than the pessary, which is not intended to damage. The PC cheeks do not press in a small area, which might produce "dimples" in the vagina walls, and might produce a reading which is too wide, leading to a pessary which might be too wide, and might cause a fitting of a pessary which causes damage to the vagina.

A typical cross sectional area for the cheeks 12 may be approximately 25 mm long by approximately 6 to 8 mm wide.

Persons skilled in the art will appreciate that a force greater than 1.1 Kg applied on the vaginal wall will cause pain and discomfort to the patient. It is noted that embodiments of the pessary of FIGS. 1D-1F are folded by a force which is greater than 1.1 Kg. In some embodiments of the present invention the PC device applies a force in the range between approximately 50 to 100 grams as a minimum, and not above approximately 1000 grams as the force extending the PC cheeks against the vaginal walls during measurement.

It is noted that in some embodiments of the invention, a kit is provided which includes a pessary, and a PC. The above kit including the PC and the pessary forms a matching set. The PC is a correct PC to use for fitting the matching pessary.

In some embodiments, double or multiple pistons may be used, as will be described further below, to provide enhanced strength, stability, and/or accuracy. According to some embodiments a pressure sensing mechanism may be used to indicate pressure being applied by the cheeks to the vaginal cavity or other internal organs or lumen. In some cases such an indicator may have a color coded indicator to indicate, for example, when the pressure is low, moderate, high and at a danger level. As can be further seen in FIG. 5C, the control mechanism may include one or more movement limiters 55, for preventing the cheeks 12 from extending too far. Optionally, there is no need for the cheeks to expand beyond a size of a maximal vagina. Optionally, there is safety in preventing the cheeks from expanding when exerting a force beyond a maximal reasonable force to be applied on vaginal walls, for example the force corresponding to the horizontal line 804 of FIG. 1C.

Reference is now made to FIGS. 6A-6D, which are simplified illustrations of still another alternative embodiment of a PC device.

FIGS. 6A-6D depict a rack and pinion cheek expansion mechanism 60 for measuring vagina size, according to some embodiments.

As can be seen in FIGS. 6A-6D, by optionally turning a knob 61, rod 62 is turned, thereby rotating the toothed pinion 63 at its distal end. The rotation of the pinion 63 causes a moving of a rack or racks 64 and rods 65. This movement of the racks 64 causes extension or retraction of the cheeks 12 according to a direction of swivel. In some embodiments, measurement of the extension of the cheeks may be indicated on a measurement indicator on the body of the PC. In further embodiments measurements may be determined according to the extent of turn or rotation of the knob 61, as depicted in the example provided in FIG. 6C. By turning the knob at the bottom of the CP device, the cheeks may be opened and closed in accordance with the scale on the knob 61.

FIG. 6B is a simplified illustration of a cross section of PC device of FIG. 6C, taken at line C.

The embodiment of FIGS. 6A-6D, as well as other embodiments of the invention which use rotation of an actuator in order to expand and retract the cheeks 12 may optionally use an electro-optic device in order to measure rotation, such as an optical encoder, or a magnetic sensor. The display of the rotation is optionally translated to distance between the cheeks 12, and optionally displayed by an electronic display.

Other embodiments included in the present invention, both embodiments which use rotation, and embodiments which use translation, optionally use optical, magnetic, and/or electronic sensors to measure, directly or indirectly, distance between the cheeks 12.

Figures 7A, 7B:
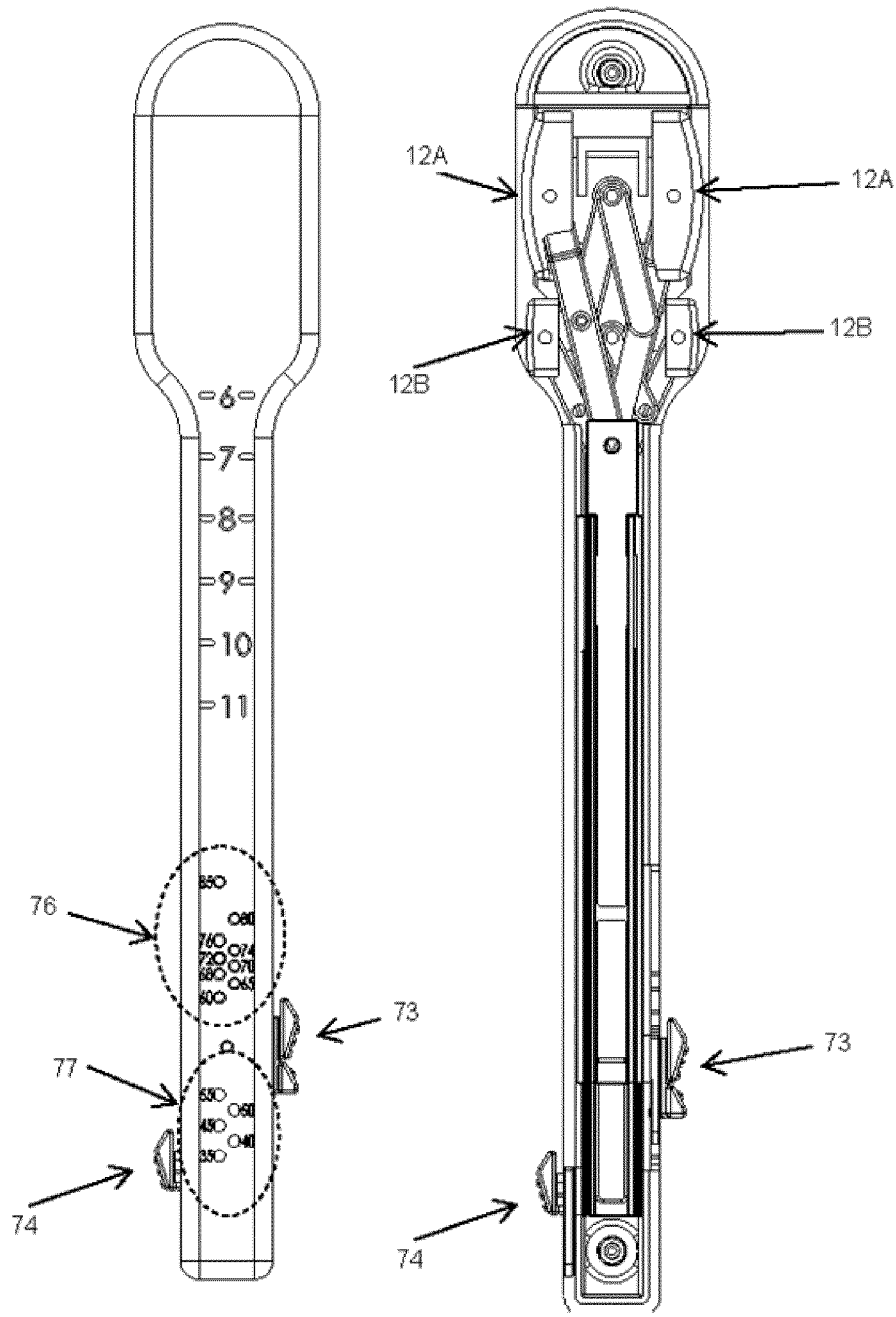
FIGS. 7A-7C are simplified illustrations of yet another alternative embodiment of a PC device.
Figure 7C:
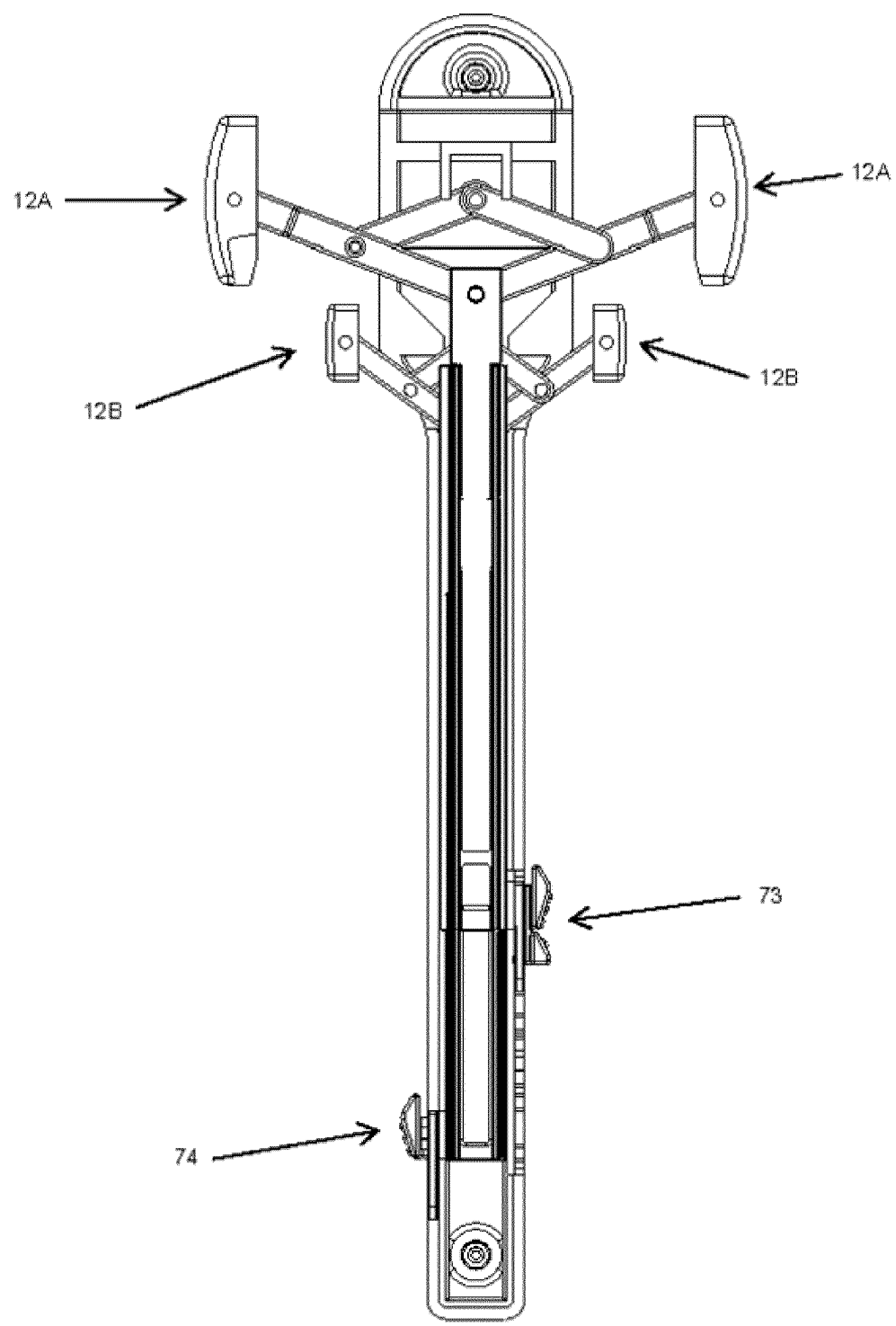

Reference is now made to FIGS. 7A-7C, which are simplified illustrations of yet another alternative embodiment of a PC device. FIGS. 7A-7C, illustrate an embodiment of the PC device, wherein a multiple set of jaws or cheeks are used.

As can be seen in FIGS. 7A-7C, multiple cheeks may be maneuvered in order to enable multiple measurements to be taken in the same examination. For example, 2 pairs of cheeks may be used, where one pair 12A measure the deep bilateral distance, which optionally corresponds to a pessary size, and a second pair 12B measure the size of the vaginal introitus, which optionally corresponds to retainment of the pessary within the vagina.

Alternatively a perineum size may be measured. Optionally, the upper pair of cheeks 12A indicates a widest diameter of a vagina, while the lower pair of cheeks 12B indicates that there is enough perineal body to keep the pessary within the vagina.

In some embodiments of the invention, the upper pair of cheeks 12A is able to expand wider than the lower pair of cheeks 12B. It is noted that in order to retain typical pessaries, the upper, or further inside, diameter of the vagina should be substantially larger than the lower, or further outside, diameter of the vagina.

In such a case as described above, the PC device optionally includes 2 controls, such as sliders 73 74, to control movement of the 2 pairs of cheeks 12A 12B, and the device body may include 2 panels or other indicators for indicating the measurement of the respective cheek pairs. For example, an upper indicator 76 may be used to indicate the size measured by the upper cheeks, and a lower indicator 77 may be used to indicate the size measured by the lower jaws 12B. Other numbers or types of cheeks, jaws or arms, as well as control mechanisms, may be used, to measure the parameters of additional or alternative targets. In some embodiments the two pairs may be operated together, by movement of one control mechanism. In other embodiments the pairs may be controlled separately, using multiple control mechanisms.

Reference is now made to FIGS. 8A-8D, which are simplified illustrations of still another alternative embodiment of a PC device. FIGS. 8A-8D depict numerous views and examples of helix type PC devices, according to some embodiments.

A connection 215 is pushed by a pusher 86 when a rod or a tube 88 is optionally advanced, either by a forward push, as with the rod 22 in FIG. 2C, or by a turn of a helix as will be described hereafter.

Figure 8C:
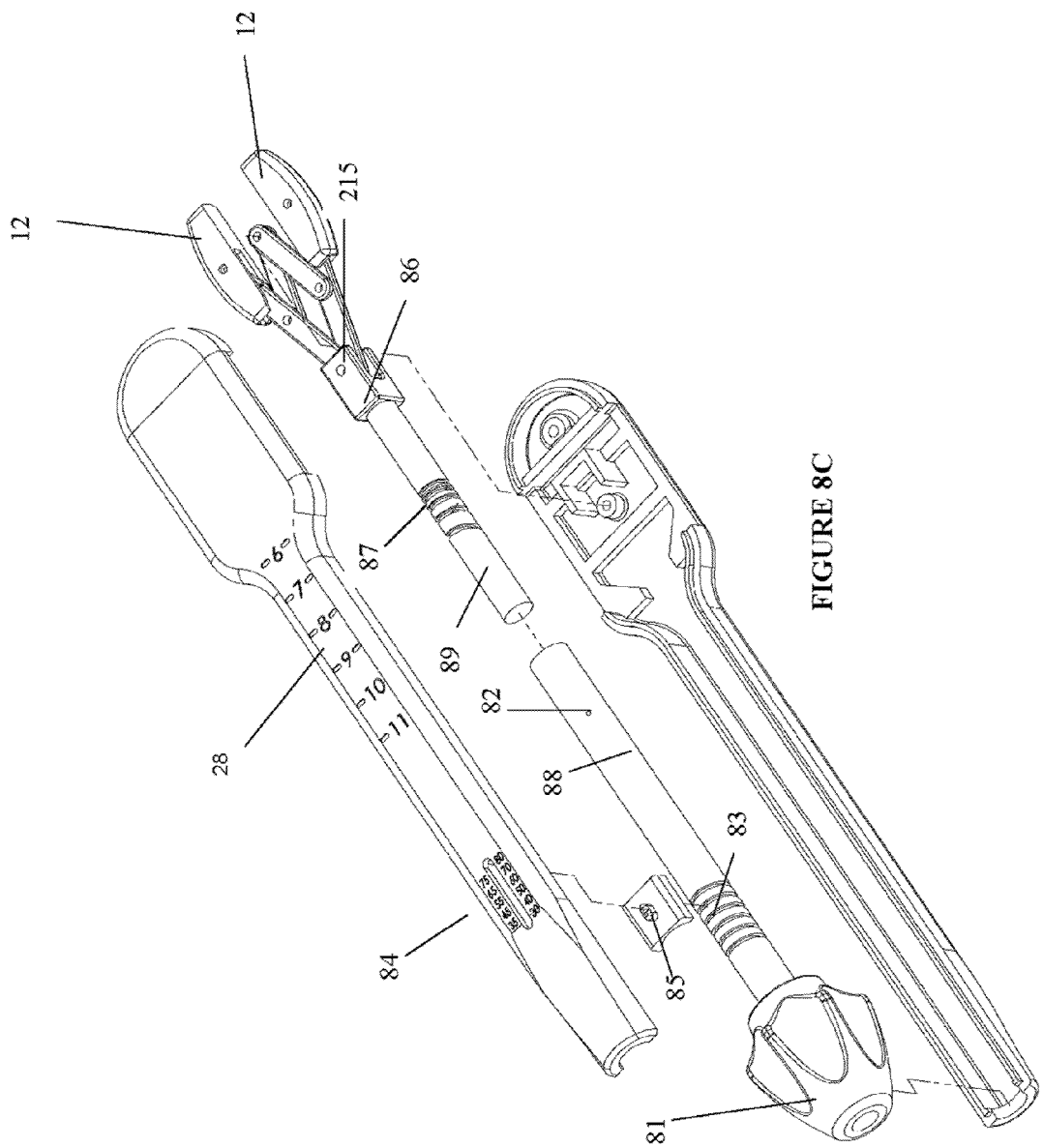
Figure 8D:
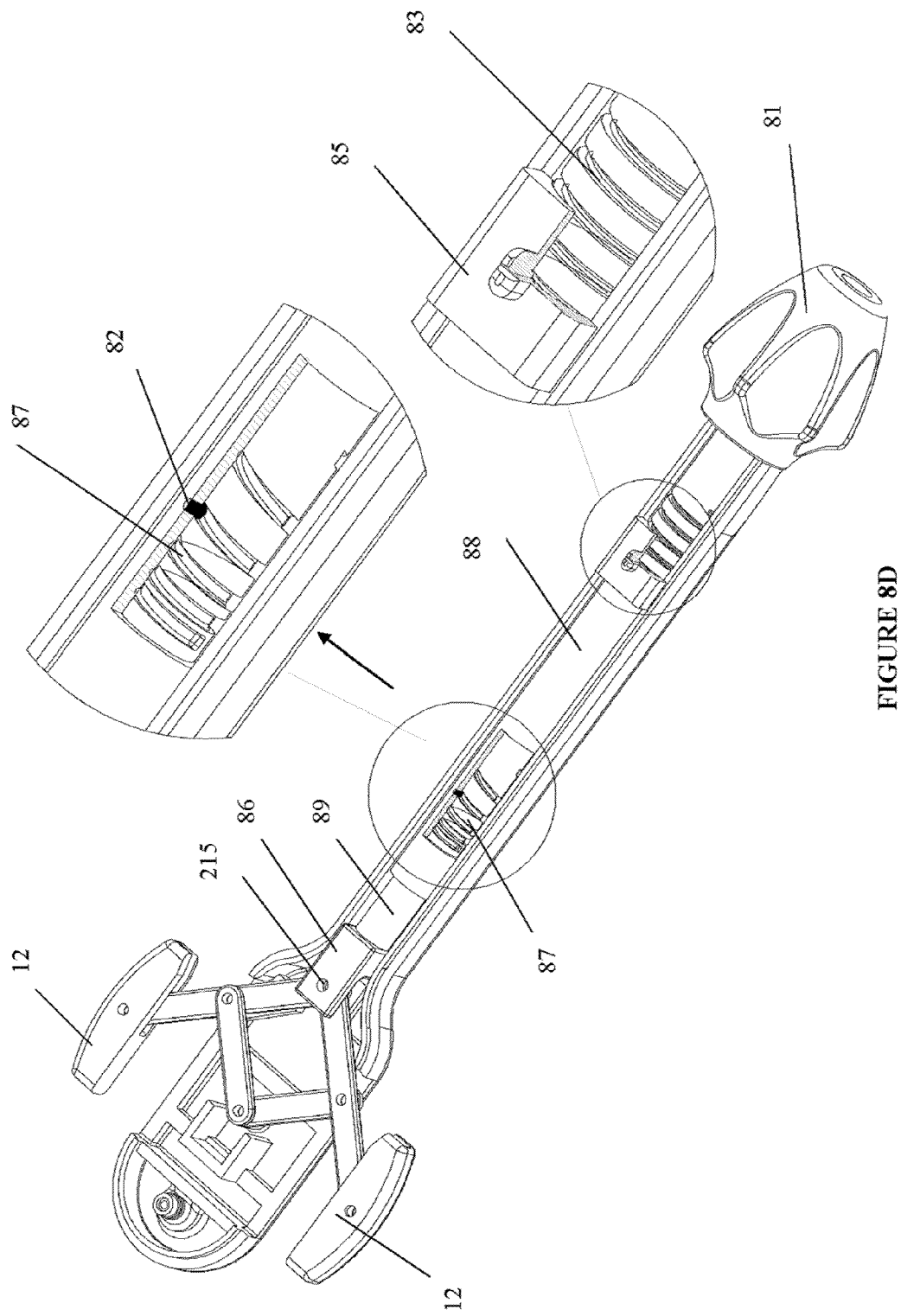
Figure 9A:
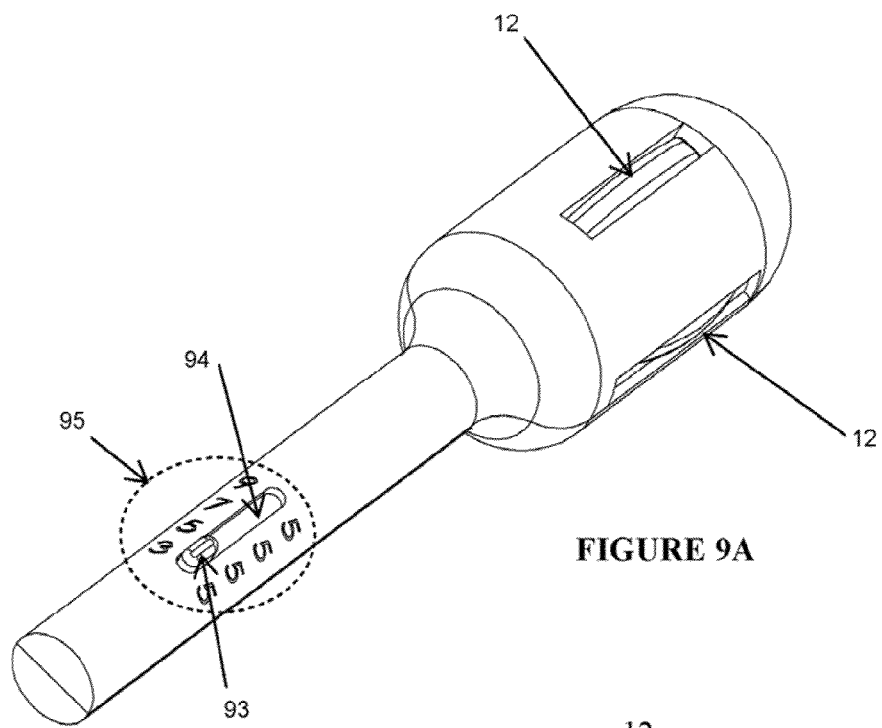
FIGS. 9A-9E are simplified illustrations of yet another alternative embodiment of a PC device.
Figure 9B:
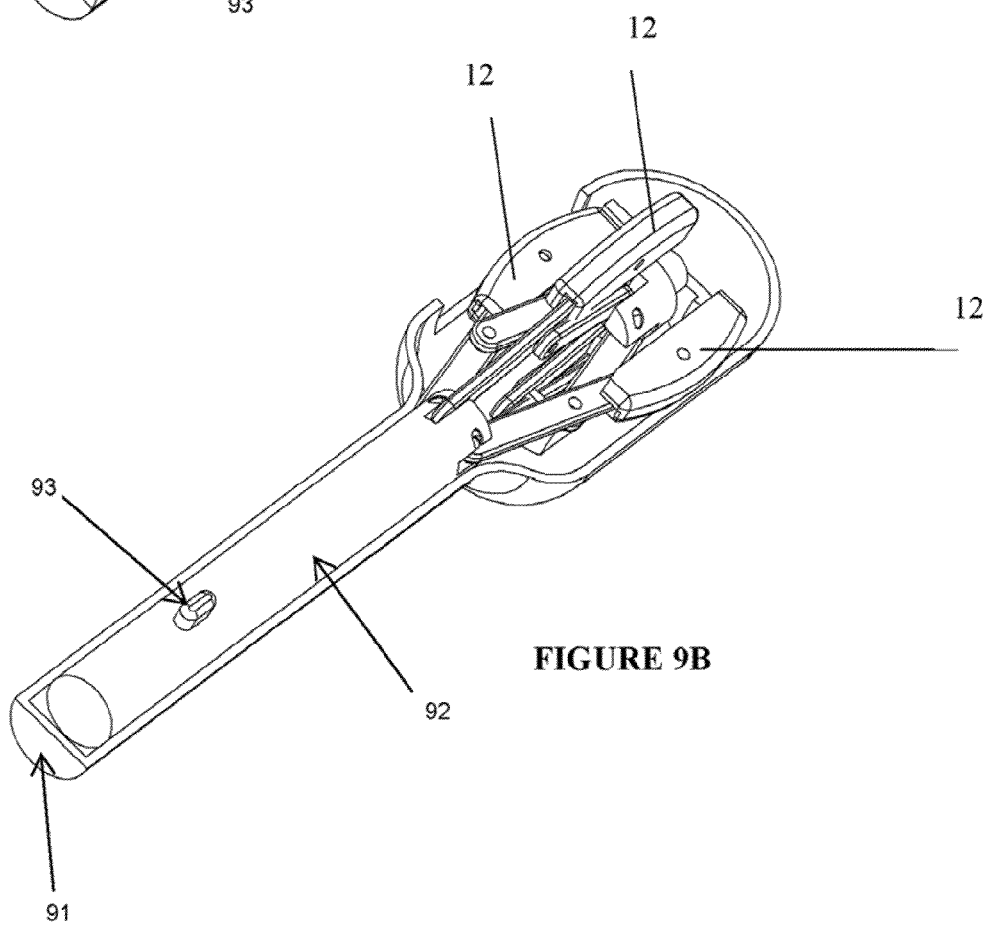
Figure 9C:
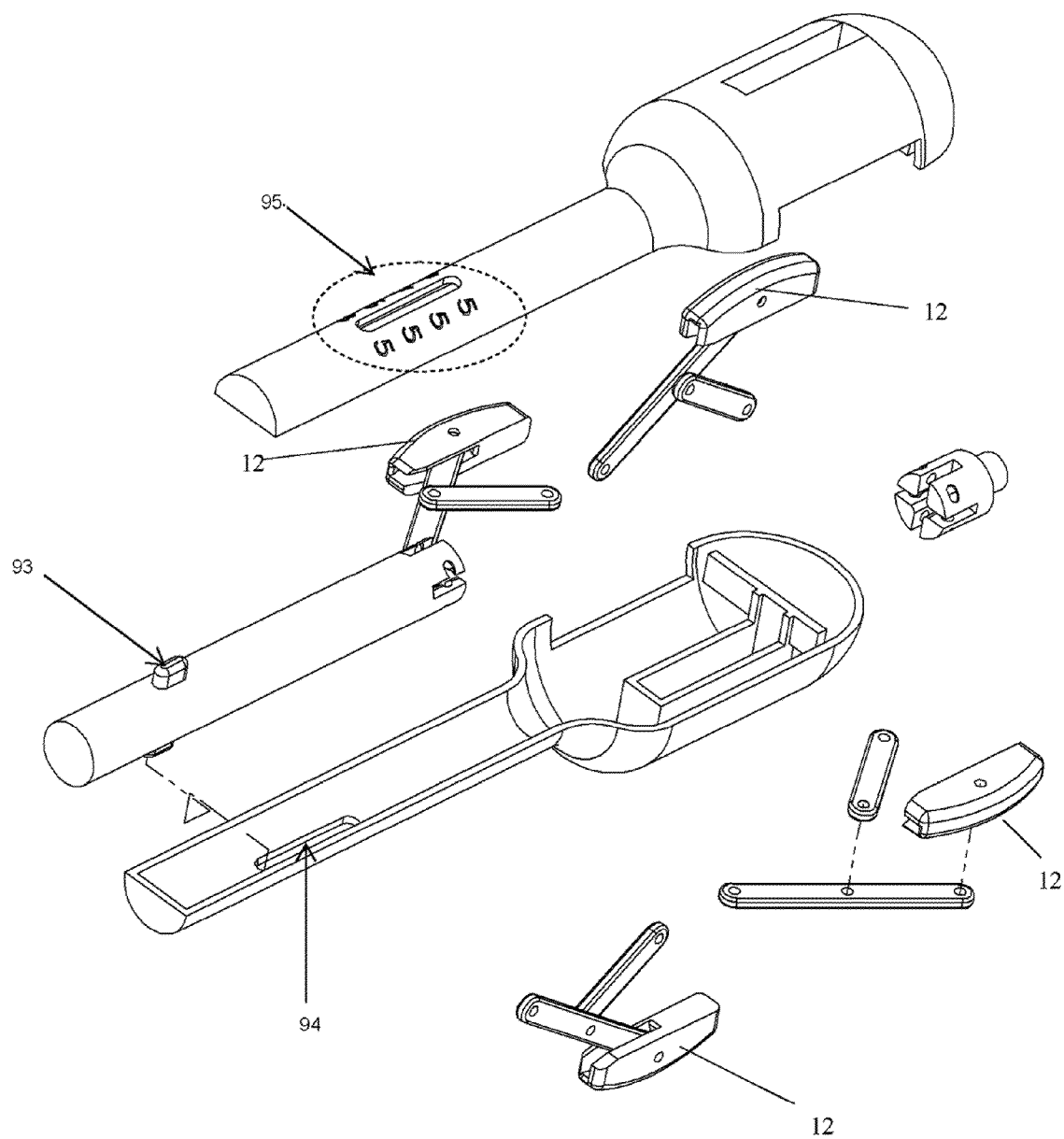
Figure 9D:
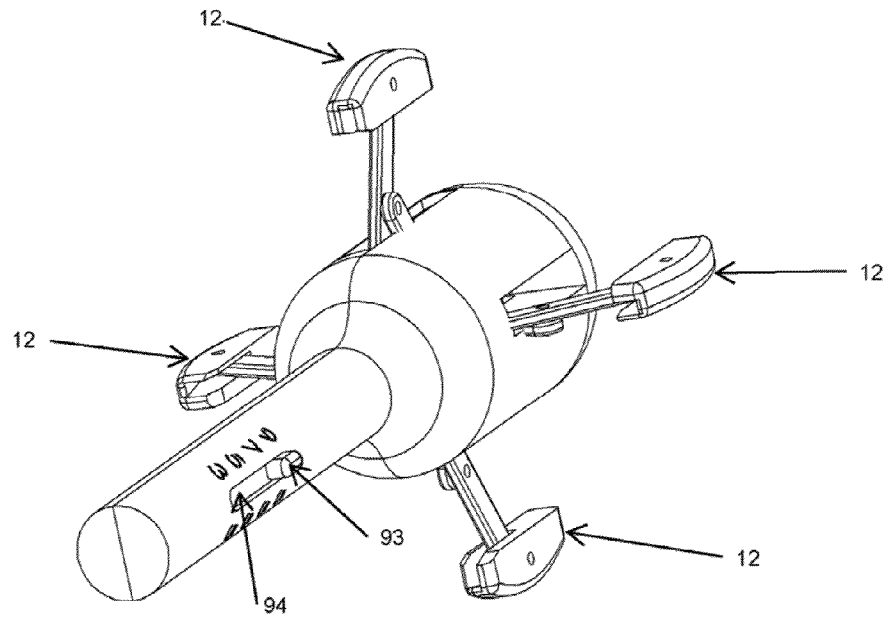
Figure 9E:
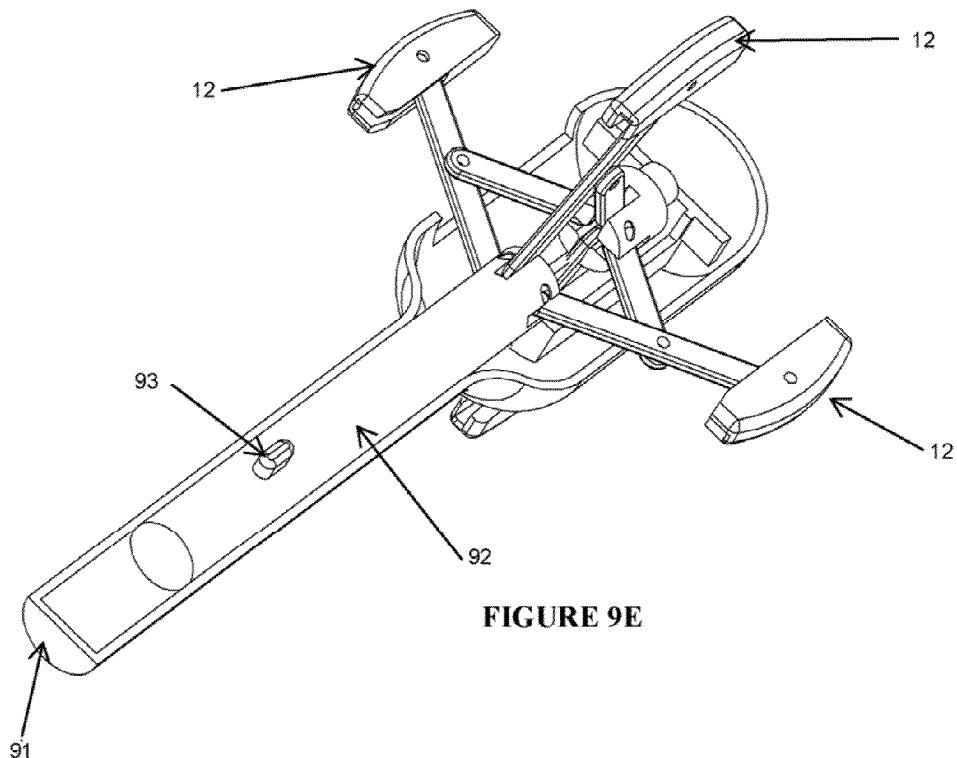

As can be seen in the figures, a slide or turn of a knob 81 optionally causes a turn of the tube 88, which has a guiding pin 82 (FIGS. 8C, 8D). A second rod 89 is optionally inserted within the distal part of the tube 88, so that the guiding pin 82 is engaged with a first helical slot 87, optionally having a variable pitch. Optional rotation of the knob 81 causes rotation of the tube 88 and the guiding pin 82 within the first helical slot 87 on the rod 89, which in turn pushes the connection 215 along a track, causing respective cheeks 12 to be opened or closed.

In one non-limiting example, each rotation of the knob 81 optionally causes a widening of the cheeks 12 to a known degree, such as each rotation increase width by 5 mm.

In some embodiments, the tube 88 may have a constant spiral pitch. A second helical slot 83 on the tube 88 is optionally advanced by each turn or rotation of the knob 81, and the progress of the second helical slot 83 may be observed by a slide indicator 85, or optionally by some other suitable indicator mechanism, such as a distance meter 84, indicating the distance between the cheeks 12.

In some embodiments, the second helical slot 83 optionally has either a constant or a variable pitch, optionally enabling a substantially uniform extension of cheeks 12 as the knob 81 is rotated. By way of a non-limiting example, each rotation of the knob 81 may initially cause a widening of the cheeks by 10 mm, however the widening-per-rotation may diminish with each subsequent rotation, representing the dynamics of the control arms and cheeks.

Reference is now made to FIGS. 9A-9E, which are simplified illustrations of yet another alternative embodiment of a PC device.

FIGS. 9A-9E show views and examples of PC device components, indicators, materials and structures, according to some embodiments.

FIGS. 9A-9E depict a PC with multiple extending arms, by way of a non-limiting example, four arms with four cheeks 12. Pushing the cheeks 12 outward using any of the means described previously, allows an examiner to gain measurements regarding one or more cross-sections of a vagina.

As opposed to previously described 2 cheek devices, which measure width within substantially one plane at a time, such as a bi-lateral distance, with the PC depicted in FIGS. 9A-9E, it is possible to measure data regarding inner circular dimensions of a hollow organ, optionally within more than one plane at a time.

In some embodiments there are optionally between 2-4 such arms and cheeks 12, and in some embodiments there may be more than 4 arms and cheeks 12. In some embodiments all arms and cheeks may be expanded and retracted together, while in other embodiments each pair of opposing arms may function as a separate unit.

A non-limiting example of a mechanism using three cheeks (not shown), is a mechanism similar to the mechanism in a drill chuck, which uses three expanding jaws to grasp a drill.

A non-limiting example embodiment (not shown), may have one expanding cheek, and the body of the PC acts as "the other cheek". The width of the vagina is the distance between the cheek and an opposing side of the PC body.

As depicted in FIGS. 9A-9E, a monitoring scale 95, a groove 94, and an indicator 93 may be used to view the opening status or progress of the cheeks 12, indicating cheek 12 extension, and thus a vagina measurement.

In some embodiments, such as depicted in FIGS. 9A-9E, the PC device body 91 is optionally smooth, and almost completely covers the operating mechanism.

The Expanding Cheeks

In some embodiments the cheeks 12 and/or other cheek support or control mechanisms are optionally constructed from plastic, metal, wood, compound materials, or any other suitable materials or combinations of materials. In some embodiments the materials include properties such as: being bio-compatible, that is, suitable for insertion into a body; non-allergenic; sturdy enough to last for several uses or even prolonged use; inexpensive enough so as not to impact a cost of manufacturing; easily cleaned of body fluids found in a vagina; and rustproof.

According to further embodiments, the cheeks 12 of the PC device may have various shapes, but preferably a rounded shape, possessing no sharp corners, to accommodate the inner lateral shape of the vagina.

Optionally, the cheeks have an ability to swivel. This may allow for better accommodation for a range of vaginal shapes, such as when opposite vaginal walls are not parallel to each other.

The Gauges and Indicators

In embodiments the size indicator may appear in various formats, such as holes which represent different sizes, colored markings which may be revealed by a position of a moving knob. In some embodiments a ruler for measuring depth of vaginal insertion and/or other target measurements or parameters may be used.

In some embodiments the PC device may be calibrated or reset during a procedure. The calibration may optionally be verified by measuring a known size, and verifying that the indicators indicate the known size, and the PC may be calibrated by adjusting the indicators to indicate the known size, if they do not.

Cleaning, Disposable Parts, and an Envelope

According to some embodiments, the PC device may be cleanable and reusable, optionally by virtue of being constructed of materials which are cleanable, optionally using soap and water as found in a home, and/or cleaning materials as found in a clinic.

The PC device is optionally operated within a flexible envelope. In some embodiments the envelope is made of a flexible material, which stretches when the cheeks expand. In such embodiments, when and if force on the cheeks is measured, the force applied by stretching the envelope is subtracted from the force measured on the cheeks. The envelope is optionally made of a bio compatible material. The envelope is optionally made of a material similar to a condom.

In some embodiments the envelope is large enough, thin and flexible enough so as not to exert force on the cheeks when the cheeks expand.

In some embodiments the envelope has a tubular shape, in some a planar shape, and/o the envelope substantially matches the shape of the PC.

The envelopes help keep the PC device clean, and the envelopes are optionally disposable.

Figure 10A:
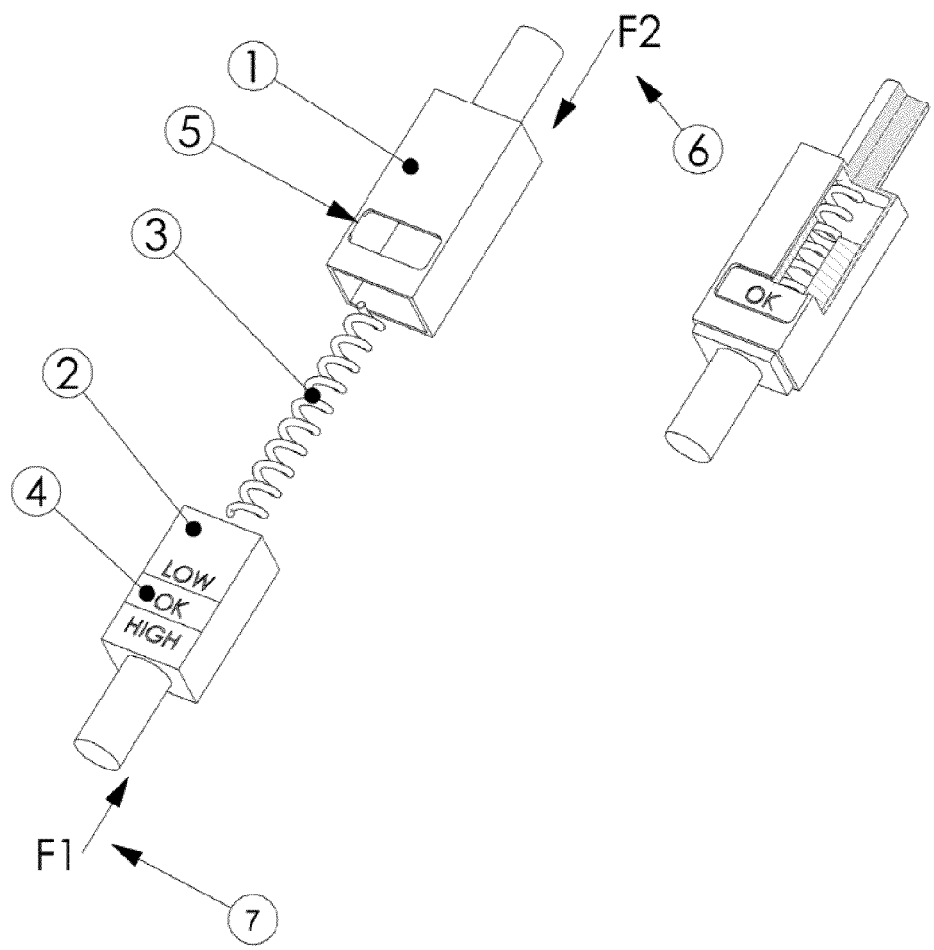
FIGS. 10A and 10B are simplified illustrations of an example PC device control mechanism according to some embodiments of the present invention.
Figure 10B:
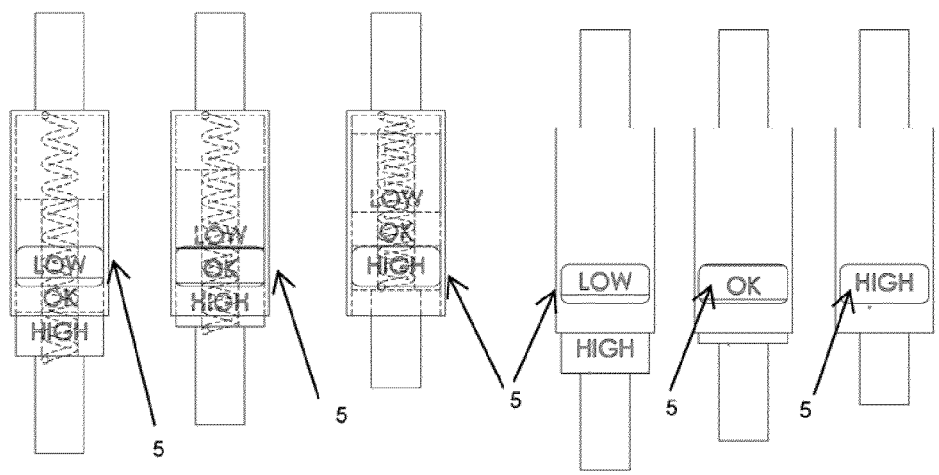

Reference is now made to FIGS. 10A and 10B, which are simplified illustrations of an example PC device control mechanism according to some embodiments of the present invention. FIGS. 10A and 10B depict a simplified illustration of a mechanism which helps to avoid application of a high force on vaginal walls, in order to avoid trauma, amongst other effects.

FIGS. 10A and 10B depict a rod 1 which is connected to a cheek opening mechanism. The rod 1 is also optionally connected to a control mechanism, such as a helix, button, lever and so on, such as, by way of a non-limiting example, described with references to previous figures. A resistance spring 3 is optionally used to determine a level of tension applied for expansion of the arms. Such tension and/or resistance is optionally measured by optionally using level indicators 4. The level indicator 4 optionally include, for example, values of "low", "ok", and "high", and/or other measurement indications.

Additionally or alternatively, a viewing window 5 may be used to observe the indicators, indicating the tension or a measure of expansion of the cheek opening mechanism.

A force F2 6 is optionally applied by the arm opening mechanism back toward a user, while a force F1 7 is optionally applied on the arm opening mechanism by the user or examiner. The forces F1 and F2 are optionally substantially equal. The force transferred through the spring 3 resulting in the opening of the cheek opening mechanism, is as a result of the force applied by the examiner using a rod 2. For example, when the force applied at the rod 2 is less than is low, the spring does not load or contract enough, failing to activate the cheek opening mechanism. In such a case the viewing window 5 and/or the level indicator 4 may indicate, for example, an indication of "low". When a substantially adequate or correct force is applied, the level indicator 4 may indicate "ok", and if too much force is applied, the level indicator 4 may indicate "high", or too much pressure.

FIG. 10B indicates 3 scenarios, one set (left) with visible measurement lines and one set (right) with invisible lines. The level of spring tension or contraction may be indicated by the "low", "ok", and "high" markings respectively.

Figure 11A:
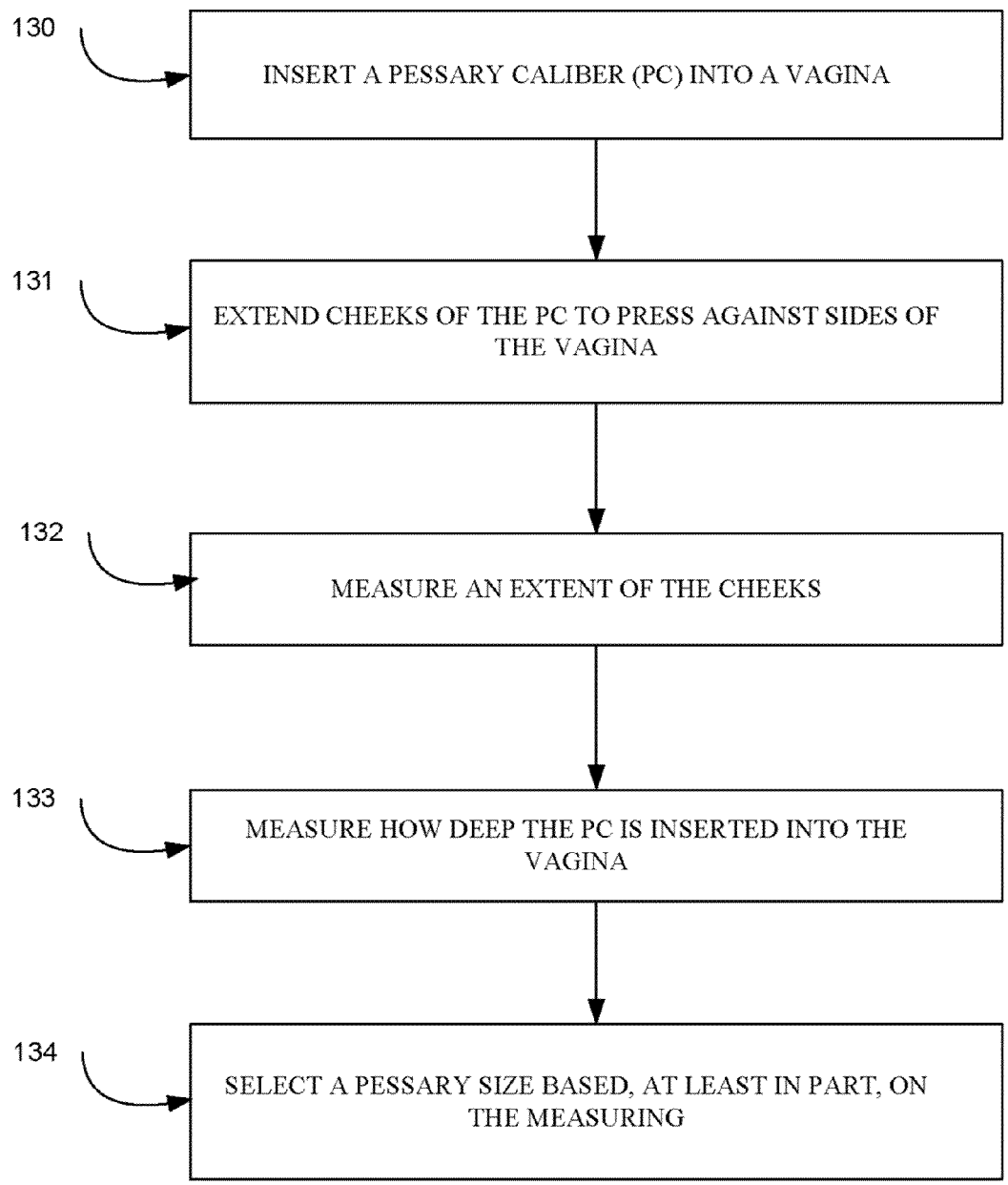
FIG. 11A is a simplified flow chart describing a process of fitting a pessary, according to some embodiments.

Reference is now made to FIG. 11A, which is a simplified flow chart describing a process of fitting a pessary, according to some embodiments. The flowchart of FIG. 11A depicts a series of operations or processes which may be implemented to measure or fit a pessary, using a PC device, according to some embodiments.

A PC device in a substantially closed state is inserted into a patient's vagina (130), such as a vagina.

Cheeks of the PC device are extended to press against sides of the vagina (131).

A practitioner and/or the patient herself (henceforth the examiner), optionally measures a distance between the cheeks (132).

The examiner optionally measures how deep the PC is inserted into the vagina (133).

The examiner optionally selects a pessary based, at least in part, on the measuring of the extent and the depth (134).

To the method described above with reference to the flow chart of FIG. 11A may be added a measurement of a pressure of the cheeks on the sides of the vagina, and optionally, the examiner selects the pessary based also on the measuring of the pressure.

It is noted that typically an experienced caretaker or practitioner is expected to operate the PC. However, optionally, a patient may operate the PC upon herself, as the controls and operating mechanism may be viewed and operated from a point of view of the patient.

Figure 11B:
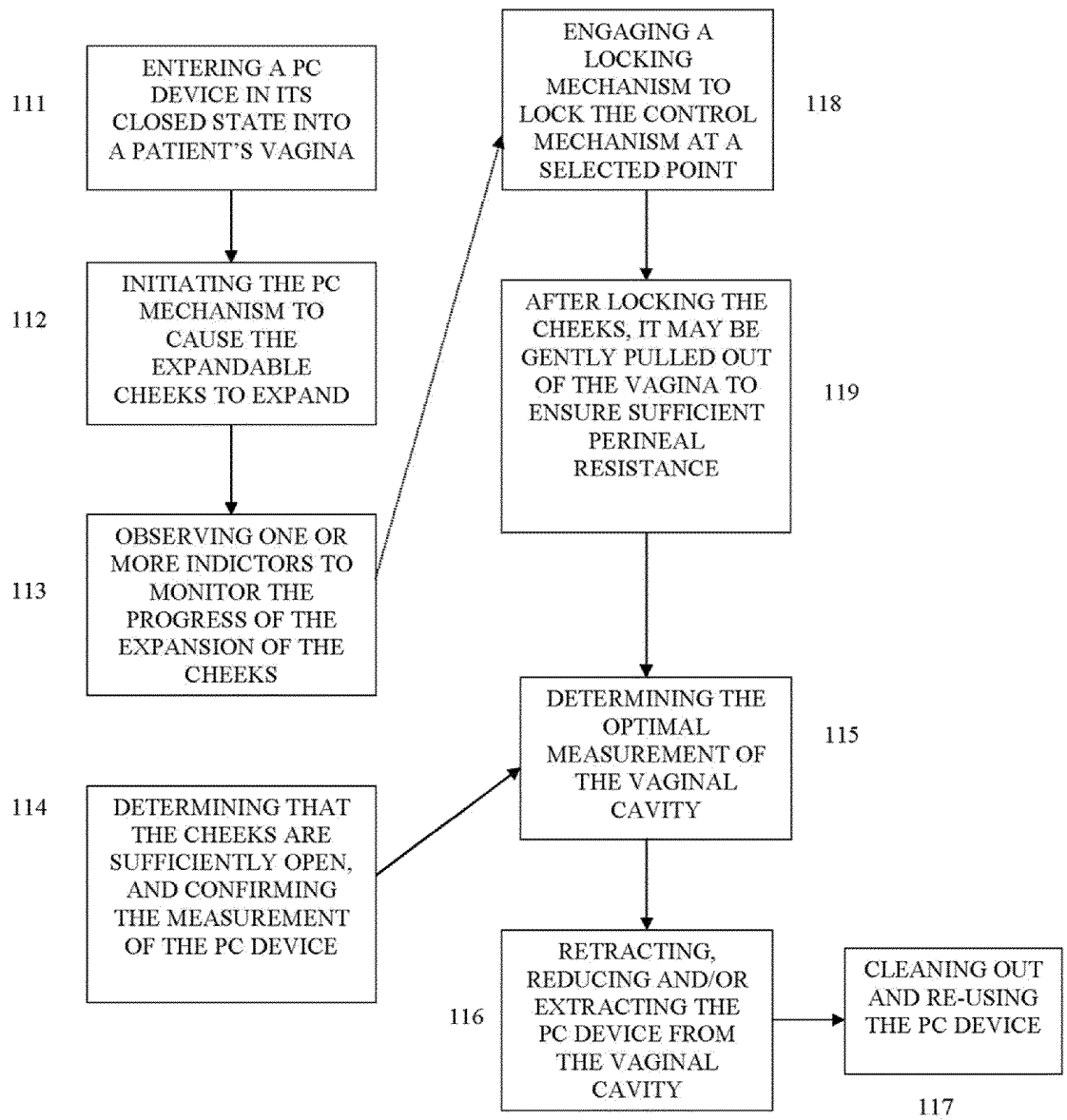
FIG. 11B is a simplified flow chart describing a process of fitting a pessary, according to other embodiments.

Reference is now made to FIG. 11B, which is a simplified flow chart describing a process of fitting a pessary, according to other embodiments.

The flowchart of FIG. 11B depicts an alternative series of operations or processes which may be implemented to measure or fit a pessary, using a PC device, according to some embodiments.

A PC device in a substantially closed state is optionally entered into a patient's vagina, such that the PC body and expandable cheeks penetrate the vaginal cavity, while the PC operating mechanism, indicators, and handle remain external to the vaginal cavity (111).

The PC control mechanism is optionally initiated, for example, by sliding, screwing or rotating the mechanism, to cause the expandable cheeks to expand (112).

A practitioner and/or the patient herself (henceforth the examiner), may observe one or more indicators to monitor the progress of the expansion of the cheeks (113).

The examiner optionally determines that the cheeks are sufficiently open and confirms that the PC device is correctly located in order to measure the vaginal cavity (114). Confirming the correct location is optionally performed by the examiner confirming the depth to which the PC device is inserted into the vagina, optionally by reading out the depth on a depth indicator. The examiner also optionally reads and optionally records the measurement indicated by the PC device. It is noted that the method applies also to other relevant target organs, lumens, and so on.

In some cases, either during or after the measurement process, the examiner may engage a locking mechanism to lock the control mechanism at a selected point, thereby locking positions of the cheeks, for measurement, testing, checking or other purposes (118)

After locking the cheeks, the examiner may gently draw or pull the device outwardly to ascertain sufficient resistance for retaining a pessary within the vagina (119).

The examiner optionally takes one or more additional measurements, optionally in rotated and/or shifted positions of the PC within the vagina, which are optionally used to determine an optimum or preferred pessary size for the patient (115).

The examiner optionally determines the optimal measurement of the PC device, based on one or more measurements of the device indicator(s) and/or pressure sensors and/or a professional experience or instinct.

Subsequently the cheeks are optionally retracted and/or reduced into the head of the PC device, and the PC device subsequently extracted from the vaginal cavity (116).

In some embodiments of the invention, the PC device may optionally be cleaned and re-used (117).

In some embodiments of the invention the materials used for producing the PC include plastics. The plastics provide advantages to the PC of a light weight relatively low cost to manufacture. In some embodiments of the invention the PC is low cost and intended for home use.

In some embodiments of the invention the materials used for producing the PC include hard wearing plastics, such as ABS, polycarbonate, and nylon, or even metal, such as stainless steel. Such embodiments may be used in a clinic situation where robustness and a long life are appreciated, and where the PC will get used many times.

In some embodiments of the invention the measurements may be performed electronically, and even optionally communicated to a computer, such as, for example, in a medical clinic setting.

In some embodiments the PC is produced of materials which may be disinfected, possible even sterilized. In some embodiments the PC is used within a sac which envelops the PC and separates the PC from the lining of the vagina. In some embodiments the sac is elastic, optionally made of materials similar to a condom, which can be inserted into a vagina and which can expand with expansion of the cheeks.

It is expected that during the life of a patent maturing from this application many forms, shapes, and sizes of relevant pessaries will be developed and the scope of the term pessary is intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The word "optionally" is used herein to mean "is provided in some embodiments and not provided in other embodiments". Any particular embodiment of the invention may include a plurality of "optional" features unless such features conflict.

As used herein the term "approximately" refers to ±25%.

It is noted that any suitable combination of the above steps may be implemented. Furthermore, other steps or series of steps may be used.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A device for measuring an inside shape of a vagina, comprising:
    a device body, operationally connected to one or more movable cheeks in a single axial plane, the one or more cheeks movable to a plurality of positions in the single axial plane in a direction transaxially relative to the device body longitudinal axis and in the single axial plane, wherein a distal portion of the device body has a symmetrical exterior shape in the single axial lane; and
    a width indicator, for indicating a distance between opposite faces of the cheeks,
    the device for measuring an inside shape of a vagina included in a kit along with an feminine incontinence treating pessary and wherein a cross sectional area of the cheeks which abuts walls of the vagina is equal to a cross sectional area of the pessary which abuts the walls of the vagina.

2. The device of claim 1 and further comprising a depth indicator, for indicating a depth of insertion of the device into the vagina.

3. The device of claim 1 and further comprising a force gage, for measuring a force by which the cheeks are pressing against the inside of the vagina.

4. The device of claim 1 in which the cheeks are shaped so as to prevent damage to vagina walls when pressing against the inside of the vagina.

5. The device of claim 1 in which the one or more movable cheeks comprise at least two cheeks, each movable in an opposite direction transaxially to the device body longitudinal axis.

6. The device of claim 1 in which the one or more movable cheeks are operationally connected to the device body by linkage of a mechanical arm for each cheek.

7. The device of claim 6 in which a rod is operationally connected to the mechanical arms, and pushing the rod causes the mechanical arms to push the movable cheeks substantially outward.

8. The device of claim 1 in which the width is indicated in terms of a pessary size.

9. The device of claim 2 in which the depth is indicated in terms of a pessary size.

10. The kit of claim 1, in which a shape of a portion of the cheeks which abuts the vaginal walls is similar to a shape of a portion of the pessary which abuts the vaginal walls.

11. The device of claim 1, in which the cheeks are expandable from an overall width of 15 mm to 95 mm.

* * * * *